(12) United States Patent
Eberlein et al.

(10) Patent No.: US 6,313,097 B1
(45) Date of Patent: *Nov. 6, 2001

(54) ANTAGONISTS OF CALCITONIN GENE-RELATED PEPTIDE

(75) Inventors: Wolfgang Eberlein, Biberach; Klaus Rudolf, Warthausen; Wolfhard Engel, Biberach; Henri Doods, Warthausen; Gerhard Hallermayer, Maselheim-Sulmingen, all of (DE)

(73) Assignee: Boehringer Ingelheim Pharma KG, Ingelheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/523,472

(22) Filed: Mar. 10, 2000

Related U.S. Application Data

(60) Provisional application No. 60/129,937, filed on Apr. 19, 1999.

(30) Foreign Application Priority Data

Mar. 2, 1999 (DE) ................................ 199 11 039

(51) Int. Cl.[7] ........................ A61K 31/454; A61K 38/05; C07D 211/00; C07K 5/065
(52) U.S. Cl. ........................ 514/19; 514/183; 514/212; 514/218; 514/241; 514/247; 514/277; 514/316; 514/331; 540/484; 540/553; 540/597; 544/215; 544/238; 544/335; 544/360; 546/184; 546/190; 546/192; 546/230; 546/233; 546/234
(58) Field of Search ................................ 514/19, 183, 212, 514/218, 241, 242, 246, 247, 248, 252, 255, 256, 257, 277, 279, 316, 317, 326, 331; 540/484, 553, 554, 555, 567, 576, 593, 597, 598; 544/180, 182, 183, 215, 233, 235, 238, 242, 253, 335, 338, 349, 360; 546/26, 112, 184, 186, 190, 192, 208, 210, 230, 233, 234

(56) References Cited

U.S. PATENT DOCUMENTS 4,826,870  5/1989  Higuchi et al. .
4,873,342  10/1989  Tanaka et al. .
5,310,743  5/1994  Schilling et al. .

FOREIGN PATENT DOCUMENTS

| 0284632 A1 | 10/1988 | (EP) . |
| 0298135 A1 | 1/1989 | (EP) . |
| 0415413 A1 | 3/1991 | (EP) . |
| 0706999 A1 | 4/1996 | (EP) . |
| 0723774 A1 | 7/1996 | (EP) . |
| WO 96/04928 A1 | 2/1996 | (WO) . |
| WO 96/15148 A2 | 5/1996 | (WO) . |
| WO 98/11128 | 3/1998 | (WO) . |
| WO 00/18764 | 4/2000 | (WO) . |

OTHER PUBLICATIONS

U.S. application No. 09/254,281, Rudolf et al., filed Oct. 12, 1999.

Primary Examiner—Jeffrey E. Russel
(74) Attorney, Agent, or Firm—R. P. Raymond; T. X. Witkowski; A. R. Stempel

(57) ABSTRACT

Compounds of the formula (I)

(I)

wherein A, R, $R^1$, $R^2$, $X^1$, $X^2$, $X^3$, and Y are as defined herein, and the tautomers and the pharmaceutically acceptable salts thereof, including pharmaceutical compositions containing these compounds, and their use in the selective antagonization of calcitonin gene-related peptide (CGRP) and in the treatment or prophylaxis of migraine or cluster headaches, non-insulin-dependent diabetes mellitus, inflammation, allergic rhinitis, asthma, morphine tolerance, menopausal hot flashes, and diseases characterized by excessive vasodilatation and consequent reduction in bloodflow.

13 Claims, No Drawings

ANTAGONISTS OF CALCITONIN GENE-RELATED PEPTIDE

RELATED APPLICATIONS

Benefit of U.S. Provisional Application Ser. No. 60/129,937, filed on Apr. 19, 1999, is hereby claimed.

DESCRIPTION OF THE INVENTION

The present invention relates to modified amino acid amides of general formula

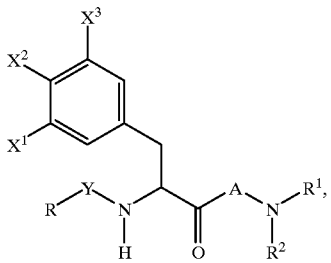

the tautomers, the diastereomers, the enantiomers, the mixtures and the salts thereof, particularly the physiologically acceptable salts thereof with inorganic or organic acids or bases, pharmaceutical compositions containing these compounds, their use and processes for preparing them.

In the above general formula I:

R denotes a 1-piperidinyl group, which is substituted in the 4 position by a mono- or di-unsaturated 5- to 7-membered aza, diaza or triaza heterocyclic group bound via a nitrogen atom, which contains one or two carbonyl groups linked to a nitrogen atom, whilst the abovementioned heterocyclic groups may be substituted at a carbon atom by an optionally substituted phenyl group, an olefinic double bond of one of the abovementioned unsaturated heterocyclic groups may be condensed with a benzene, pyridine, diazine, 1,3-oxazole, thiophene, furan, thiazole, pyrrole, N-methyl-pyrrole, quinoline, imidazole or N-methyl-imidazole ring or two olefinic double bonds in one of the abovementioned unsaturated heterocyclic groups may be benzocondensed, and wherein the abovementioned phenyl group as well as the benzo-, thieno-, pyrido- and diazino-condensed heterocyclic groups may additionally be mono-, di- or trisubstituted in the carbon skeleton by fluorine, chlorine or bromine atoms, by alkyl groups, cycloalkyl groups with 3 to 8 carbon atoms, nitro, alkoxy, alkylthio, alkylsulfinyl, alkylsulfonyl, alkylsulfonylamino, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluoromethylthio, trifluoromethylsulfinyl or trifluoromethylsulfonyl groups, whilst the substituents may be identical or different, Y denotes the divalent groups

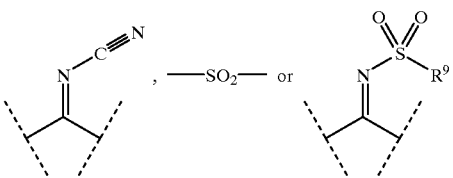

wherein $R^9$ denotes an alkyl group with 1 to 4 carbon atoms or a phenyl group optionally substituted by a halogen atom or a methyl or methoxy group, $X^1$, $X^2$ and $X^3$, which may be identical or different, denote the hydrogen atom, the fluorine, chlorine or bromine atom, a branched or unbranched alkyl group, an alkoxy, trifluoromethyl, dialkylaminoalkyl, dialkylaminoalkoxy, nitro, hydroxy, amino, acetylamino, methylsulfonyloxy, aminocarbonyl, alkylaminocarbonyl, dialkylaminocarbonyl, alkanoyl, cyano, trifluoromethoxy, trifluoromethylthio, trifluoromethylsulfinyl or trifluoromethylsulfonyl group, A denotes a bond or the divalent group

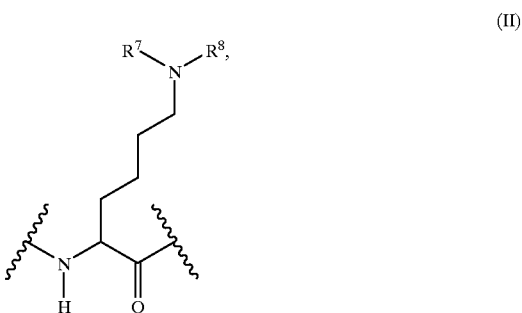

linked via the —CO group to the $NR^1R^2$ group of formula I, wherein $R^7$ denotes the hydrogen atom or the methyl group, $R^8$ denotes the hydrogen atom, the methyl, methoxycarbonyl, ethoxycarbonyl, n-propoxycarbonyl, isopropoxycarbonyl, tert-butoxycarbonyl or acetyl group, $R^1$ denotes the hydrogen atom, an alkyl group with 1 to 7 carbon atoms, which may be substituted in the ω position by a cyclohexyl, phenyl, pyridinyl, diazinyl, hydroxy, amino, alkylamino, dialkylamino, carboxy, aminocarbonyl, aminocarbonylamino, acetylamino, 1-pyrrolidinyl, 1-piperidinyl, 4-(1-piperidinyl)-1-piperidinyl, 4-morpholinyl, hexahydro-1H-1-azepinyl, [bis-(2-hydroxyethyl)]amino, 4-alkyl-1-piperazinyl or 4-(ω-hydroxyalkyl)-1-piperazinyl group, a phenyl or pyridinyl group, whilst the abovementioned heterocyclic groups and phenyl groups may additionally be mono-, di- or trisubstituted in the carbon skeleton by fluorine, chlorine or bromine atoms, by methyl, alkoxy, trifluoromethyl, hydroxy, amino, acetylamino, aminocarbonyl, cyano, methylsulfonyloxy, trifluoromethoxy, trifluoromethylthio, trifluoromethylsulfinyl or trifluoromethylsulfonyl groups and the substituents may be identical or different, $R^2$ denotes the hydrogen atom or an alkyl group with 1 to 3 carbon atoms optionally substituted by a phenyl or pyridinyl group or $R^1$ and $R^2$ together with the included nitrogen atom denote a group of general formula III

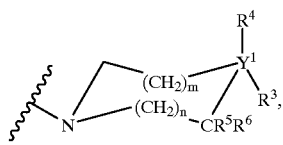

(III)

wherein

Y$^1$ denotes the carbon atom or, if R$^4$ denotes a free pair of electrons, it may also represent the nitrogen atom, m denotes the numbers 0, 1 or 2, n denotes the numbers 0, 1 or 2, R$^3$ denotes the hydrogen atom, an amino, alkylamino, dialkylamino, alkyl, cycloalkyl, aminoalkyl, alkylaminoalkyl, dialkylaminoalkyl, aminoiminomethyl, aminocarbonylamino, alkylaminocarbonylamino, cycloalkylaminocarbonylamino, phenylaminocarbonylamino, aminocarbonylalkyl, aminocarbonylaminoalkyl, alkoxycarbonyl, alkoxycarbonylalkyl, carboxyalkyl or carboxy group, a phenyl, pyridinyl, diazinyl, 1-naphthyl, 2-naphthyl, pyridinylcarbonyl or phenylcarbonyl group, each of which may be mono-, di- or trisubstituted in the carbon skeleton by fluorine, chlorine or bromine atoms, by alkyl, alkoxy, methylsulfonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(dialkylamino)alkyl, ω-(dialkylamino)hydroxyalkyl, ω-(carboxy)alkanoyl, trifluoromethoxy, trifluoromethylthio, trifluoromethylsulfinyl or trifluoromethylsulfonyl groups, whilst the substituents may be identical or different, a 4- to 10-membered azacycloalkyl group, a 5- to 10-membered oxaza, thiaza or diazacycloalkyl group, or a 6- to 10-membered azabicycloalkyl group, whilst the abovementioned mono- and bicyclic heterocyclic groups are bound via a nitrogen or carbon atom, a 1-alkyl-4-piperidinylcarbonyl or 4-alkyl-1-piperazinylcarbonyl group, whilst the abovementioned mono- and bicyclic heterocyclic groups as well as the 1-alkyl-4-piperidinylcarbonyl and 4-alkyl-1-piperazinylcarbonyl group may be substituted in the ring by an alkyl group with 1 to 7 carbon atoms, by an alkanoyl, dialkylamino, phenylcarbonyl, pyridinylcarbonyl, carboxyalkanoyl, carboxyalkyl, alkoxycarbonylalkyl, alkoxycarbonyl, aminocarbonyl, alkylaminocarbonyl, alkylsulfonyl, cycloalkyl or cycloalkylalkyl group, by a cycloalkylcarbonyl, azacycloalkylcarbonyl, diazacycloalkylcarbonyl or oxazacycloalkylcarbonyl group optionally alkyl-substituted in the ring, whilst the alicyclic moieties contained in these substituents contain 3 to 10 ring members and the heteroalicyclic moieties each contain 4 to 10 ring members and the abovementioned phenyl and pyridinyl groups may in turn be mono-, di- or trisubstituted by fluorine, chlorine or bromine atoms, by alkyl, alkoxy, methylsulfonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(carboxy)alkanoyl, trifluoromethoxy, trifluoromethylthio, trifluoromethylsulfinyl or trifluoromethylsulfonyl groups, whilst the substituents may be identical or different, or R$^3$ together with R$^4$ and Y$^1$ denote a 4- to 7-membered cycloaliphatic ring, in which a methylene group may be replaced by a group —NH— or —N(alkyl)-, whilst a hydrogen atom bound to a nitrogen atom within the group R$^3$ may be replaced by a protecting group, R$^4$ denotes a hydrogen atom, an alkyl group with 1 to 4 carbon atoms, whilst an unbranched alkyl group may be substituted in the ω position by a phenyl, pyridinyl, diazinyl, amino, alkylamino, dialkylamino, 1-pyrrolidinyl, 1-piperidinyl, 4-methyl-1-piperazinyl, 4-morpholinyl or hexahydro-1H-1-azepinyl group, an alkoxycarbonyl, the cyano or aminocarbonyl group or a free pair of electrons, if Y$^1$ denotes a nitrogen atom, and R$^5$ and R$^6$ each denote a hydrogen atom or, if Y$^1$ is a carbon atom, R$^4$ together with R$^6$ also denotes another carbon-carbon bond, whilst R$^3$ is as hereinbefore defined and R$^5$ denotes a hydrogen atom or if Y$^1$ is a carbon atom, R$^4$ together with R$^6$ also denotes a further carbon-carbon bond and R$^3$ together with R$^5$ and the enclosed double bond denotes a partially hydrogenated or aromatic five- to seven-membered, mono- or bicyclic carbocyclic or heterocyclic group, whilst all the abovementioned alkyl and alkoxy groups as well as the alkyl groups present within the other groups mentioned may contain 1 to 7 carbon atoms, unless otherwise specified, and all the abovementioned cycloalkyl groups as well as the cycloalkyl groups present within the other groups mentioned may, unless otherwise specified, contain 5 to 10 carbon atoms.

For example, R$^3$ may denote the 1-pyrrolidinyl, 1-piperidinyl, 4-(dimethylamino)-1-piperidinyl, 4-piperidinyl or 4-morpholinyl group, whilst the nitrogen atom of the 4-piperidinyl group may be substituted by an alkanoyl or alkyl group with 1 to 4 carbon atoms in each case or by a methylsulfonyl group, the hexahydro-1H-1-azepinyl, 8-methyl-8-azabicyclo[3,2,1]oct-3-yl, 4-alkyl-1-piperazinyl, hexahydro-4-alkyl-1H-1,4-diazepin-1-yl, 1-alkyl-4-piperidinylcarbonyl or 4-alkyl-1-piperazinylcarbonyl group.

For example, R may denote 4-(1,3-dihydro-4-phenyl-2(2H)-oxoimidazol-1-yl)-1-piperidinyl, 4-(1,3-dihydro-2(2H)-oxobenzimidazol-1-yl)-1-piperidinyl, 4-[2,4(1H,3H)-dioxoquinazolin-3-yl]-1-piperidinyl, 4-(1,3-dihydro-2(2H)-oxoimidazo[4,5-b]pyridin-3-yl, 4-(3,4-dihydro-2(1H)-oxoquinazolin-3-yl)-1-piperidinyl, 4-(2,3,4,5-tetrahydro-2(1H)-oxo-1,3-benzodiazepin-3-yl)-1-piperidinyl, 4-(7-methoxy-2,3,4,5-tetrahydro-2(1H)-oxo-1,3-benzodiazepin-3-yl)-1-piperidinyl, 4-[2(1H)-oxoquinolin-3-yl]-1-piperidinyl, 4-(2,4-dihydro-5-phenyl-3(3H)-oxo-1,2,4-triazol-2-yl)-1-piperidinyl, 4-(1,3-dihydro-2(2H)-oxoimidazo[4,5-c]quinolin-3-yl)-1-piperidinyl or 4-(5,7-dihydro-6-oxo-dibenzo[d,f][1,3]diazepin-5-yl)-1-piperidinyl group.

The protecting groups mentioned in the preceding and following definitions include those protecting groups which are familiar in peptide chemistry, particularly a phenylalkoxycarbonyl group with 1 to 3 carbon atoms in the alkoxy moiety, optionally substituted in the phenyl nucleus by a halogen atom, by a nitro or phenyl group, or by one or two methoxy groups, for example the benzyloxycarbonyl, 2-nitro-benzyloxycarbonyl, 4-nitro-benzyloxycarbonyl, 4-methoxy-benzyloxycarbonyl, 2-chlorobenzyloxycarbonyl, 3-chloro-benzyloxycarbonyl, 4-chloro-benzyloxycarbonyl, 4-biphenylyl-α,α-dimethyl-benzyloxycarbonyl or 3,5-dimethoxy-α,α-dimethyl-benzyloxycarbonyl group, an alkoxycarbonyl group with a total of 1 to 5 carbon atoms in the alkyl moiety, for example the methoxycarbonyl, ethoxycarbonyl, n-propoxycarbonyl, isopropoxycarbonyl, n-butoxycarbonyl, 1-methylpropoxycarbonyl, 2-methylpropoxycarbonyl or tert-butyloxycarbonyl group, the allyloxycarbonyl, 2,2,2-trichloroethoxycarbonyl or 9-fluorenylmethoxycarbonyl group or the formyl, acetyl or trifluoroacetyl group.

The present invention relates to racemates where the compounds of general formula I have only one chiral element. However, the application also includes the individual diastereomeric pairs of antipodes or mixtures thereof which occur if there is more than one chiral element in the compounds of general formula I.

Particularly preferred are the compounds of general formula I which are in the D- or (R)-configuration with regard to the amino acid partial structure of formula

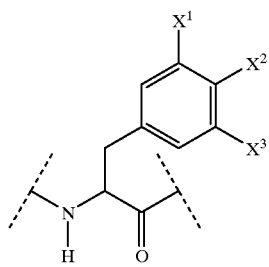

(IV)

and are in the L- or (S)-configuration with regard to the amino acid partial structure of formula II which may be present in the group A.

The compounds of general formula I have valuable pharmacological properties based on their ability to selectively antagonize calcitonin gene-related peptide (CGRP). The invention further relates to pharmaceutical compositions containing these compounds, their use and the preparation thereof.

Preferred compounds of the above general formula I are those wherein

R denotes the 1-piperidinyl group, which is substituted in the 4 position by a mono- or di-unsaturated 5- to 7-membered aza, diaza or triaza heterocyclic group, bound via a nitrogen atom, which contains one or two carbonyl groups linked to a nitrogen atom, whilst the abovementioned heterocyclic groups are optionally substituted at a carbon atom by a phenyl group, an olefinic double bond of one of the abovementioned unsaturated heterocyclic groups may be condensed with a benzene, pyridine or quinoline ring or two olefinic double bonds in one of the abovementioned unsaturated heterocyclic groups may be benzocondensed, and whilst the abovementioned condensed heterocyclic groups is optionally mono-, di- or trisubstituted in the carbon skeleton, the phenyl groups contained in these groups, or both, by fluorine, chlorine or bromine atoms, by $C_{1-3}$-alkyl, trifluoromethyl, $C_{1-3}$-alkoxy, hydroxy, amino, nitro, phenyl, carboxy, methoxycarbonyl, ethoxycarbonyl, aminocarbonyl, methylaminocarbonyl, hydroxyethylaminocarbonyl, (4-morpholinyl)carbonyl, (1-piperidinyl)carbonyl or (4-methyl-1-piperazinyl)carbonyl groups, whilst the substituents are identical or different and multiple substitution with the three latter substituents is excluded, and monosubstitution is particularly preferred and the $C_{1-3}$-alkyl, $C_{1-3}$-alkoxy and phenyl group are especially preferred as substituents, Y denotes the divalent groups

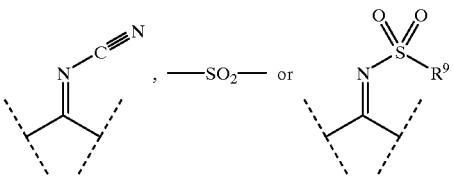

wherein $R^9$ denotes a $C_{1-3}$-alkyl group or a phenyl group optionally substituted by a fluorine, chlorine or bromine atom, or a methyl or methoxy group, $X^1$, $X^2$ and $X^3$, which may be identical or different, denote the hydrogen atom, the fluorine, chlorine or bromine atom, a $C_{1-3}$-alkyl, $C_{1-3}$-alkoxy, trifluoromethyl, hydroxy, amino or acetylamino group, A denotes a bond or the divalent group

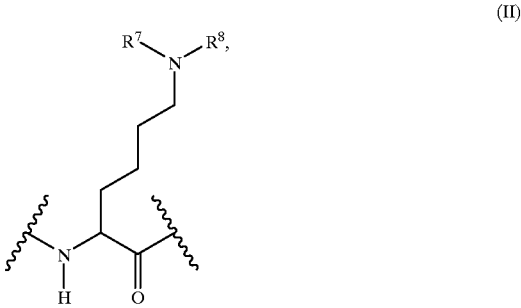

(II)

linked to the $NR^1R^2$ group of formula I via the —CO group, wherein $R^7$ and $R^8$ independently of each other in each case denote the hydrogen atom or the methyl group, $R^1$ denotes the hydrogen atom or an alkyl group with 1 to 4 carbon atoms optionally substituted in the ω position by an amino, methylamino, dimethylamino or 4-(1-piperidinyl)-1-piperidinyl group, $R^2$ denotes the hydrogen atom, the methyl or ethyl group or $R^1$ and $R^2$ together with the enclosed nitrogen atom denote a group of general formula

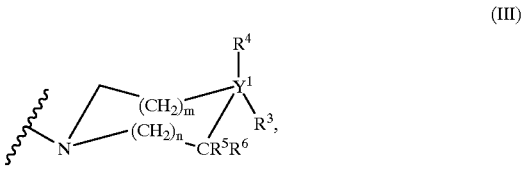

(III)

wherein $Y^1$ denotes the carbon atom or, if $R^4$ denotes a free pair of electrons, it may also represent the nitrogen atom, m denotes the numbers 0 or 1, n denotes the numbers 1 or 2, $R^3$ denotes the hydrogen atom, a phenyl, pyridinyl or diazinyl group, each of which may be substituted in the carbon skeleton by a fluorine, chlorine or bromine atom or by a methyl or methoxy group, a 5- to 7-membered azacycloalkyl group, a 5- to 7-membered oxaza or diazacycloalkyl group or a 7- to 9-membered azabicycloalkyl group, whilst the abovementioned mono- and bicyclic heterocyclic groups are bound via a nitrogen or carbon atom and may be substituted by an alkyl group with 1 to 3 carbon atoms, by a $C_{1-4}$-alkanoyl, di-$C_{1-3}$-alkylamino or $C_{1-3}$-alkylsulfonyl group, $R^4$ denotes a hydrogen atom, an alkyl group with 1 to 3 carbon atoms, whilst an unbranched alkyl group may be substituted in the ω position by a phenyl or pyridinyl group, or a free pair of electrons, if $Y^1$ denotes a nitrogen atom, and $R^5$ and $R^6$ in each case denote a hydrogen atom, the tautomers, the diastereomers, the enantiomers, the mixtures and the salts thereof.

Particularly preferred compounds of the above general formula I are those wherein R denotes the 1-piperidinyl group which is substituted in the 4 position by a 1,3-dihydro-4-phenyl-2(2H)-oxoimidazol-1-yl, 1,3-dihydro-2(2H)-oxobenzimidazol-1-yl, 2,4(1H,3H)-dioxoquinazolin-3-yl, 1,3-dihydro-2(2H)-oxoimidazo[4,5-b]pyridin-3-yl, 3,4-dihydro-2(1H)-oxoquinazolin-3-yl, 2,3,4,5-tetrahydro-2(1H)-oxo-1,3-benzodiazepin-3-yl, 2(1H)-oxoquinolin-3-yl, 2,4-dihydro-5-phenyl-3(3H)-oxo-1,2,4-triazol-2-yl, 1,3-dihydro-2(2H)-oxoimidazo[4,5-c]quinolin-3-yl or 5,7-dihydro-6-oxo-dibenzo[d,f][1,3]diazepin-5-yl group, whilst the abovementioned bicyclic heterocyclic groups may be mono-, di- or trisubstituted in the carbon skeleton and/or at the phenyl groups contained in these groups by fluorine, chlorine or bromine atoms, by methyl, trifluoromethyl, methoxy, hydroxy, amino, nitro, phenyl, phenylmethyl, carboxy, methoxycarbonyl, ethoxycarbonyl, aminocarbonyl, methylaminocarbonyl, hydroxyethylaminocarbonyl, (4-morpholinyl)carbonyl, (1-piperidinyl)carbonyl or (4-methyl-1-piperazinyl)carbonyl groups, whilst the substituents may be identical or different and multiple substitution with the three latter substituents is ruled out, and monosubstitution is particularly preferred and the methyl, methoxy and phenyl groups are particularly preferred as substituents, Y denotes the divalent groups

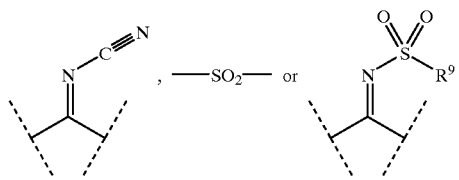

wherein $R^9$ denotes the methyl group or the phenyl group, $X^1$ denotes the fluorine, chlorine or bromine atom or the methyl group, $X^2$ denotes the fluorine, chlorine or bromine atom, the methyl, methoxy, hydroxy or amino group, $X^3$ denotes the fluorine, chlorine or bromine atom or the methyl group, A denotes a bond or the divalent group

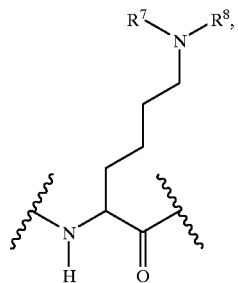

(II)

linked to the $NR^1R^2$ group of formula I via the —CO group, wherein $R^7$ and $R^8$ denote hydrogen atoms, $R^1$ and $R^2$ together with the enclosed nitrogen atom denote a group of general formula

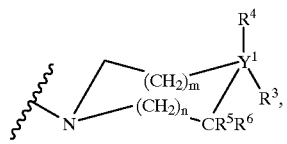

(III)

wherein $Y^1$ denotes the carbon atom or, if $R^4$ denotes a free pair of electrons, it may also represent the nitrogen atom, m denotes the number 1, n denotes the number 1, $R^3$ denotes a phenyl or pyridinyl group, each of which may be substituted in the carbon skeleton by a fluorine, chlorine or bromine atom, or by a methyl or methoxy group, a 1-pyrrolidinyl, 1-piperidinyl, 4-(dimethylamino)-1-piperidinyl, 4-piperidinyl or 4-morpholinyl group, whilst the nitrogen atom of the 4-piperidinyl group may be substituted by an alkyl group with 1 to 2 carbon atoms in each case, a hexahydro-1H-1-azepinyl, 4-methyl-1-piperazinyl or 4-ethyl-1-piperazinyl group, $R^4$ denotes a hydrogen atom, an alkyl group with 1 or 2 carbon atoms or a free pair of electrons, if $Y^1$ denotes a nitrogen atom, and $R^5$ and $R^6$ in each case denote a hydrogen atom, the tautomers, the diastereomers, the enantiomers, the mixtures and the salts thereof.

The following are mentioned as examples of particularly preferred compounds:

(1) 1-[4-amino-3,5-dibromo-N-[[4-(3,4-dihydro-2(1H)-oxoquinazolin-3-yl)-1-piperidinyl]methylsulfonyliminomethyl]-D-phenylalanyl]-4-(1-piperidinyl)-piperidine, (2) 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-piperidinyl)-piperidine, (3) 1-[4-amino-3,5-dibromo-N-[[4-(3,4-dihydro-2(1H)-oxoquinazolin-3-yl)-1-piperidinyl]phenylsulfonyliminomethyl]-D-phenylalanyl]-4-(1-piperidinyl)-piperidine, (4) 1-[3,5-dibromo-N-[[4-(3,4-dihydro-2(1H)-oxoquinazolin-3-yl)-1-piperidinyl]cyanoiminomethyl]-D-tyrosyl]-4-(1-piperidinyl)-piperidine, (5) 1-[N²-[3,5-dibromo-N-[[4-(3,4-dihydro-2(1H)-oxoquinazolin-3-yl)-1-piperidinyl]methylsulfonyliminomethyl]-D-tyrosyl]-L-lysyl]-4-(4-pyridinyl)piperazine, (6) 1-[N²-[3,5-dibromo-N-[[4-(3,4-dihydro-2(1H)-oxoquinazolin-3-yl)-1-piperidinyl]phenylsulfonyliminomethyl]-D-tyrosyl]-L-lysyl]-4-(4-pyridinyl)piperazine, (7) 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-methyl-4-piperidinyl)-piperidine, (8) 1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-piperidinyl)-piperidine, (9) 1-[3,5-dibromo-N-[[4-(3,4-dihydro-2(1H)-oxoquinazolin-3-yl)-1-piperidinyl]cyanoiminomethyl]-D-tyrosyl]-4-(4-pyridinyl)piperazine,

(10) 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(4-pyridinyl)piperazine,

(11) 1-[3,5-dibromo-N-[[4-(3,4-dihydro-2(1H)-oxoquinazolin-3-yl)-1-piperidinyl]cyanoiminomethyl]-D-tyrosyl]-4-(1-methyl-4-piperidinyl)-piperidine,

(12) 1-[3,5-dibromo-N-[[4-[3,4-dihydro-2(1H)-oxoquinazolin-3-yl]-1-piperidinyl]cyanoiminomethyl]-D-tyrosyl]-4-(4-methyl-1-piperazinyl)piperidine,

(13) 1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-methyl-4-piperidinyl)piperidine,

(14) 1-[4-amino-3,5-dibromo-N-[[4-[1,3-dihydro-4-phenyl-2(2H)-oxoimidazol-1-yl]-1-piperidinyl]cyanoiminomethyl]-D-phenyl-alanyl]-4-(4-methyl-1-piperazinyl)piperidine,

(15) 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(4-methyl-1-piperazinyl)piperidine,

(16) 1-[4-amino-3,5-dibromo-N-[[4-(2,4-dihydro-5-phenyl-3(3H)-oxo-1,2,4-triazol-2-yl)-1-piperidinyl]cyanoiminomethyl]-D-phenylalanyl]-4-(1-piperidinyl)-piperidine,

(17) 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(1-piperidinyl)-piperidine,

(18) 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-piperidinyl)-piperidine,

(19) 1-[3,5-dibromo-N-[[4-(2,3,4,5-tetrahydro-2(1H)-oxo-1,3-benzodiazepin-3-yl)-1-piperidinyl]cyanoiminomethyl]-D-tyrosyl]-4-(1-piperidinyl)-piperidine,

(20) 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-methyl-4-piperidinyl)piperazine,

(21) 1-[3,5-dibromo-N-[[4-(2,3,4,5-tetrahydro-2(1H)-oxo-1,3-benzodiazepin-3-yl)-1-piperidinyl]cyanoiminomethyl]-D-tyrosyl]-4-(1-methyl-4-piperidinyl)piperazine,

(22) 1-[4-amino-3,5-dibromo-N-[[4-(2,4-dihydro-5-phenyl-3(3H)-oxo-1,2,4-triazol-2-yl)-1-piperidinyl]cyanoiminomethyl]-D-phenylalanyl]-4-(1-methyl-4-piperidinyl)piperazine,

(23) 1-[4-amino-3,5-dibromo-N-[[4-(2,3,4,5-tetrahydro-2(1H)-oxo-1,3-benzodiazepin-3-yl)-1-piperidinyl]cyanoiminomethyl]-D-phenylalanyl]-4-(1-methyl-4-piperidinyl)piperazine,

(24) 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(1-methyl-4-piperidinyl)-piperidine,

(25) 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(1-piperidinyl)-piperidine,

(26) 1-[3,5-dibromo-N-[[4-(3,4-dihydro-2(1H)-oxoquinazolin-3-yl)-1-piperidinyl]cyanoiminomethyl]-4-methyl-D,L-phenylalanyl]-4-(4-pyridinyl)piperazine,

(27) 1-[4-amino-3,5-dibromo-N-[[4-[1,3-dihydro-2(2H)-oxoimidazo[4,5-c]quinolin-3-yl]-1-piperidinyl]cyanoiminomethyl]-D-phenylalanyl]-4-(1-piperidinyl)piperidine,

(28) 1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(1-piperidinyl)-piperidine,

(29) 1-[4-amino-3,5-dibromo-N-[[4-(5,7-dihydro-6-oxodibenzo[d,f][1,3]-diazepin-5-yl)-1-piperidinyl]cyanoiminomethyl]-D-phenylalanyl]-4-(1-piperidinyl)-piperidine,

(30) 1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(1-methyl-4-piperidinyl)piperazine,

(31) 1-[4-amino-3,5-dibromo-N-[[4-[1,3-dihydro-2(2H)-oxo-imidazo[4,5-c]quinolin-3-yl]-1-piperidinyl]cyanoiminomethyl]-D-phenylalanyl]-4-(1-methyl-4-piperidinyl)piperazine,

(32) 1-[4-amino-3,5-dibromo-N-[[4-(2,3,4,5-tetrahydro-2(1H)-oxo-1,3-benzodiazepin-3-yl)-1-piperidinyl]sulfonyl]-D-phenylalanyl]-4-(1-methyl-4-piperidinyl)piperazine,

(33) 1-[3,5-dibromo-N-[[4-(7-methoxy-2,3,4,5-tetrahydro-2(1H)-oxo-1,3-benzodiazepin-3-yl)-1-piperidinyl]cyanoiminomethyl]-D-tyrosyl]-4-(1-piperidinyl)piperidine,

(34) 1-[3,5-dibromo-N-[[4-(7-methoxy-2,3,4,5-tetrahydro-2(1H)-oxo-1,3-benzodiazepin-3-yl)-1-piperidinyl]cyanoiminomethyl]-D-tyrosyl]-4-(1-methyl-4-piperidinyl)piperazine,

(35) 1-[3,5-dibromo-N-[[4-[1,3-dihydro-2(2H)-oxoimidazo[4,5-c]quinolin-3-yl]-1-piperidinyl]cyanoiminomethyl]-D-tyrosyl]-4-(1-piperidinyl)piperidine,

(36) 1-[3,5-dibromo-N-[[4-[1,3-dihydro-2(2H)-oxoimidazo[4,5-c]quinolin-3-yl]-1-piperidinyl]cyanoiminomethyl]-D-tyrosyl]-4-(1-methyl-4-piperidinyl)piperazine,

(37) 1-[4-amino-3,5-dibromo-N-[[4-(7-methoxy-2,3,4,5-tetra-hydro-2(1H)-oxo-1,3-benzodiazepin-3-yl)-1-piperidinyl]cyanoiminomethyl]-D-phenylalanyl]-4-(4-methyl-1-piperazinyl)-piperidine and

(38) 1-[4-amino-3,5-dibromo-N-[[4-[1,3-dihydro-2(2H)-oxoimidazo[4,5-c]quinolin-3-yl]-1-piperidinyl]cyanoiminomethyl]-D-phenylalanyl]-4-(4-methyl-1-piperazinyl)piperidine and the salts thereof.

The compounds of general formula I are prepared by methods known in principle, using processes derived from peptide chemistry (cf., for example, Houben-Weyl, Methoden der Organischen Chemie, Vol. 15/2). The amino protecting groups used may be those described in Houben-Weyl, Methoden der Organischen Chemie, Vol. 15/1, preferably urethane protecting groups such as, e.g., the fluorenylmethoxycarbonyl, phenylmethoxycarbonyl or tert-butyloxycarbonyl group. Any functional groups present in the group A of the compounds of general formula I or in their precursors are additionally protected, to prevent side reactions, by suitable protecting groups (cf for example: G. B. Fields et al., Int. J. Peptide Protein Res. 35, 161 (1990); T. W. Greene, Protective Groups in Organic Synthesis). Examples of amino acids protected in their side chains in this way include, in particular, Lys(Boc), Lys(Cl-Z) and Lys(Teoc), which are generally commercially available, in some cases in the form of their derivatives.

Instead of protecting amino groups in the side chains, it is also possible to use amino acids which carry precursor functions and are substituted particularly by nitro or cyano in their side chain, or derivatives thereof, for example 5-cyano-norvaline.

After the synthesis of the N- and C-terminally substituted amino acid derivative, any protecting groups present in the side chains of α-amino acid partial structures are finally hydrogenolytically cleaved with suitable reagents which are also known in principle from the literature, e.g., aryl-methoxycarbonyl protecting groups, for example with hydrogen in the presence of palladium black and using glacial acetic acid as solvent.

Any precursor functions present in the side chain of the α-amino acid may also finally be converted into the desired amino functions by hydrogenolysis; nitroalkyl groups yield aminoalkyl groups, under conditions familiar to the chemist, while the cyano group is converted into the aminomethyl group.

The following methods are particularly suitable for preparing the compounds of general formula I according to the invention:

a) In order to prepare compounds of general formula I wherein Y denotes one of the divalent iminomethyl groups

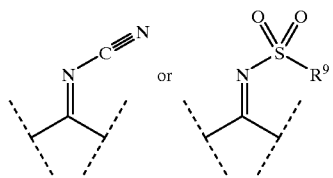

wherein $R^9$ is defined as specified hereinbefore:

Reacting compounds of general formula

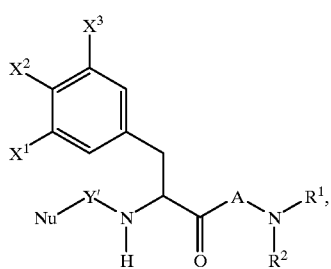

(V)

wherein A, $R^1$, $R^2$, $X^1$, $X^2$ and $X^3$ are as hereinbefore defined, Y' denotes one of the two iminomethyl groups specified above and Nu is a leaving group, for example an alkoxy, aryloxy, alkylthio, alkylsulfinyl or alkylsulfonyl group with in each case up to 10 carbon atoms, e.g., the methoxy, ethoxy, phenyloxy, methylthio, ethylthio, methylsulfinyl, ethylsulfinyl, propylsulfinyl, isopropylsulfinyl, methylsulfonyl or ethylsulfonyl group, the chlorine or bromine atom, the $SO_2H$, $SO_3H$ or $OPOCl_2$ group, but preferably the phenoxy group, with secondary amines of general formula

R—H       (VI), wherein R is as hereinbefore defined.

The reactions are carried out analogously to methods known from the literature (cf G. B. L. Smith, J. Amer. Chem. Soc. 51, 476 [1929]; B. Rathke, Chem. Ber. 17, 297 [1884]; R. Phillips and H. T. Clarke, J. Amer. Chem. Soc. 45, 1755 [1923]; S. J. Angyal and W. K. Warburton, J. Amer. Chem. Soc. 73, 2492 [1951]; H. Lecher and F. Graf, Chem. Ber. 56, 1326 [1923]; J. Wityak, S. J. Gould, S. J. Hein and D. A. Keszler, J. Org. Chem. 52, 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51, 1882–1884 [1986]; A. E. Miller and J. J. Bischoff, Synthesis 1986, 777; R. A. B. Bannard, A. A. Casselman, W. F. Cockburn and G. M. Brown, Can. J. Chem. 36, 1541 [1958]; Aktieselskabet Grea, Kopenhagen, DE2826452-C2; K. Kim, Y. T. Lin and H. S. Mosher, Tetrah. Letters 29, 3183–3186 [1988]; H. B. Arzeno et al., Synth. Commun. 20, 3433–3437 [1990]; H. Bredereck and K. Bredereck, Chem. Ber. 94, 2278 [1961]; H. Eilingsfeld, G. Neubauer, M. Seefelder and H. Weidinger, Chem. Ber. 97, 1232 [1964]; P. Pruszynski, Can. J. Chem. 65, 626 [1987]; D. F. Gavin, W. J. Schnabel, E. Kober and M. A. Robinson, J. Org. Chem. 32, 2511 [1967]; N. K. Hart, S. R. Johns, J. A. Lamberton and R. I. Willing, Aust. J. Chem. 23, 1679 [1970]; CIBA Ltd., Belgian Patent 655403; Chem. Abstr. 64, 17481 [1966]; J. P. Greenstein, J. Org. Chem. 2, 480 [1937]; F. L. Scott and J. Reilly, J. Amer. Chem. Soc. 74, 4562 [1952]; W. R. Roush and A. E. Walts, J. Amer. Chem. Soc. 106, 721 [1984]; M. S. Bernatowicz, Y. Wu and G. R. Matsueda, J. Org. Chem. 57, 2497–2502 [1992]; H. Tsunematsu, T. Imamura and S. Makisumi, J. Biochem. 94, 123–128 [1983]; R. Mohr, A. Buschauer and W. Schunack, Arch. Pharm. 321, 221–227 [1988]; K. Atwal, F. N. Ferrara and S. Z. Ahmed, Tetrah. Lett. 35, 8085–8088 [1994]; P. J. Garratt, C. J. Hobbs and R. Wrigglesworth, J. Org. Chem. 54, 1062–1069 [1989]; P. J. Garratt and S. N. Thorn, tetrahedron 49, 6885–6898 [1993]) at temperatures between 0° C. and +100° C., preferably +40° C. and +80° C., and using inert solvents, for example dichloromethane, tetrahydrofuran, 1,4-dioxane, acetonitrile, dimethylformamide, 2-pentanol, dimethylacetamide, N-methylpyrrolidone or mixtures thereof and generally in the presence of auxiliary bases, particularly alkali metal carbonates such as sodium or potassium carbonate, or tertiary amines, preferably N-ethyl-diisopropylamine or triethylamine.

b) In order to prepare compounds of general formula I wherein Y denotes the divalent group —$SO_2$—:

Reacting compounds of general formula

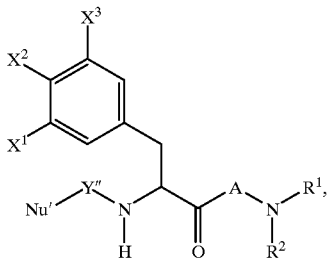

(VII)

wherein A, $R^1$, $R^2$, $X^1$, $X^2$ and $X^3$ are as hereinbefore defined, Y" denotes the $SO_2$ group and Nu' is a leaving group, for example a halogen atom, such as the chlorine, bromine or iodine atom, an alkyl or arylsulfonyloxy group or an alkoxy group with in each case up to 10 carbon atoms, e.g., the methoxy or ethoxy group, or a phenoxy or naphthoxy group optionally mono-, di- or trisubstituted by chlorine or bromine atoms or by methyl, nitro or hydroxy groups, whilst the substituents may be identical or different, with secondary amines of general formula

R—H  (VI), wherein R is as hereinbefore defined, and, if necessary, subsequently cleaving any protecting groups or modifying precursor functions using the methods described hereinbefore.

If in general formula VII Nu' denotes a halogen atom, an alkyl or arylsulfonyloxy group, the reaction is carried out under Schotten-Baumann or Einhorn conditions, i.e., the components are reacted in the presence of at least one equivalent of an auxiliary base at temperatures between −50° C. and +120° C., preferably −10° C. and +100° C., and optionally in the presence of solvents. Suitable auxiliary bases preferably include alkali metal and alkaline earth metal hydroxides, for example sodium hydroxide, potassium hydroxide, alkali metal carbonates, e.g., sodium carbonate, potassium carbonate or cesium carbonate, alkali metal acetates, e.g., sodium or potassium acetate, as well as tertiary amines, for example pyridine, 2,4,6-trimethylpyridine, quinoline, triethylamine, N-ethyldiisopropylamine, N-ethyldicyclohexylamine, 1,4-diazabicyclo[2,2,2]octane or 1,8-diazabicyclo[5,4,0]undec-7-ene, whilst suitable solvents include for example dichloromethane, tetrahydrofuran, 1,4-dioxane, acetonitrile, dimethylformamide, dimethylacetamide, N-methylpyrrolidone or mixtures thereof; if alkali metal or alkaline earth metal hydroxides, alkali metal carbonates or acetates are used as auxiliary bases, water may also be added to the reaction mixture as cosolvent.

The nucleofugic group Nu' used in compounds of general formula VII is the 2-hydroxyphenoxy group, whilst the preferred solvent used for the reaction with amines of general formula VI is boiling dioxane.

The intermediate products of the reaction are the non-isolatable azasulfenes of general formula

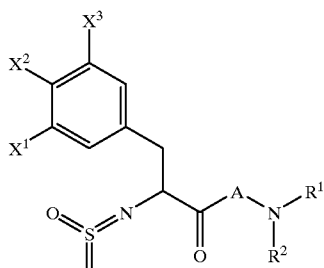

(VIII)

The converted amino acids of general formula I according to the invention contain at least one chiral centre. If the group A is also chiral, the compounds may also occur in the form of two diastereomeric pairs of antipodes. The invention includes the individual isomers as well as the mixtures thereof.

The diastereomers are separated on the basis of their different physicochemical properties, e.g., by fractional crystallization from suitable solvents, by high pressure liquid or column chromatography using chiral or preferably achiral stationary phases.

The racemates of general formula I may be separated for example by HPLC on suitable chiral stationary phases (e.g., Chiral AGP, Chiralpak A D). Racemates which contain a basic or acidic function can also be separated via the diastereomeric, optically active salts, which are formed on reacting with an optically active acid, for example (+)-or (−)-tartaric acid, (+) or (−)-diacetyltartaric acid, (+) or (−)-monomethyltartrate or (+)-camphorsulfonic acid, or an optically active base, for example with (R)-(+)-1-phenylethylamine, (S)-(−)-1-phenylethylamine or (S)-brucine.

According to a conventional method of isomer separation, the racemate of a compound of general formula I is reacted with one of the abovementioned optically active acids or bases in equimolar amounts in a solvent and the crystalline, diastereomeric, optically active salts obtained are separated, using their different solubilities. This reaction may be carried out in any kind of solvent, provided that it shows a sufficient difference in the solubility of the salts. Preferably, methanol, ethanol or mixtures thereof, for example in a ratio by volume of 50:50, are used. Then each of the optically active salts is dissolved in water, neutralized with a base such as sodium carbonate or potassium carbonate, sodium hydroxide solution or potassium hydroxide solution and in this way the corresponding free compound is obtained in the (+) or (−) form.

However, only the (R)-enantiomer or a mixture of two optically active diastereomeric compounds coming under general formula I will be obtained if the methods of synthesis described above are carried out in each case with a suitable (R)-configured reaction component.

The starting materials of general formulae V, VI and VII needed to synthesize the compounds of general formula I are prepared analogously to methods known from the literature.

Starting compounds of general formula V may be obtained for example by reacting the phenylalanine derivatives of general formula

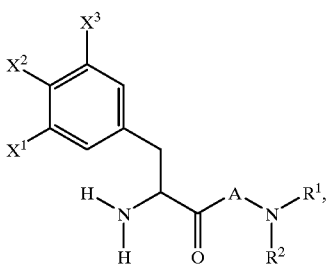

(IX)

described in WO 98/11128, wherein A, $R^1$, $R^2$, $X^1$, $X^2$ and $X^3$ are as hereinbefore defined, with iminocarbonates of general formula Nu-Y'-Nu" (X), wherein Nu and Y' are defined as in a) above and Nu", which may be different from Nu or the same as Nu, may have the same meanings as Nu. The reactions are carried out analogously to the data provided by R. Mohr, A. Buschauer and W. Schunack, Arch. Pharm. 321, 221–227 [1988] or A. Buschauer, Arch. Pharm. 320, 377–380 [1987] or P. J. Garratt and S. N. Thorn, Tetrahedron 49, 6885–6898 [1993].

Compounds of general formula VI have generally already been described in WO 98/11128. The compound

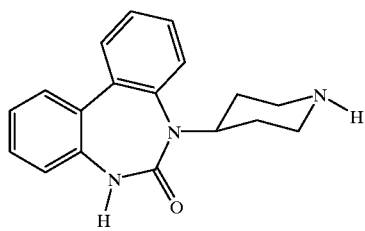

(XI)

which comes under general formula VI and has not previously been described can easily be prepared from 2-amino-2'-nitrobiphenyl by reductive amination with 1-(phenylmethyl)-4-piperidone, subsequent reduction of the nitro group, cyclization using N,N'-carbonyldiimidazole and hydrogenolytic removal of the benzyl group by methods known from the literature.

The compounds of general formula VII required as starting compounds may be obtained from phenylalanine derivatives of general formula IX as hereinbefore defined by reacting with sulfates of general formula Nu'-Y"-Nu''' (XII)

wherein Nu' and Y" are defined as in b) hereinbefore and Nu''', which may be different from Nu' or identical to Nu', may have the same meanings as Nu'. The preferred sulfate is the cyclic compound

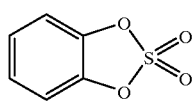

(XIII)

(cf also: G. E. DuBois and R. A. Stephenson, J. Org. Chem. 45, 5371–5373 [1980]).

The compounds of general formula I obtained may be converted into their physiologically acceptable salts with inorganic or organic acids, particularly for pharmaceutical use. Suitable acids for this purpose include for example hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid.

In addition, if the new compounds of formula I obtained contain an acid function, for example a carboxy group, they may, if desired, be converted into their addition salts with inorganic or organic bases, particularly physiologically acceptable addition salts suitable for pharmaceutical use. Bases which may be used include, for example, sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have CGRP-antagonistic properties and display good affinities in CGRP-receptor binding studies. The compounds exhibit CGRP-antagonistic properties in the pharmacological test systems described hereinafter.

The following trials were conducted to demonstrate the affinity of compounds of general formula I for human CGRP receptors and their antagonistic properties:

A. Binding Studies with SK-N-MC cells (Expressing the Human CGRP Receptor)

SK-N-MC cells are cultivated in "Dulbecco's modified Eagle Medium". The medium is removed from confluent cultures. The cells are washed twice with PBS buffer (Gibco 041-04190 M), detached by the addition of PBS buffer mixed with 0.02% EDTA, and isolated by centrifugation. After resuspension in 20 mL of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH7.40] the cells are twice centrifuged at 100×g and resuspended in BSS. After the cell count has been determined the cells are homogenized using an Ultra-Turrax and centrifuged for 10 minutes at 3000×g. The supernatant is discarded and the pellet is recentrifuged and resuspended in Tris buffer (10 mM Tris, 50 mM NaCl, 5 mM MgCl$_2$, 1 mM EDTA, pH 7.40), enriched with 1% bovine serum albumin and 0.1% bacitracin (1 mL/1000000 cells). The homogenized preparation is frozen at −80° C. The membrane preparations are stable under these conditions for more than 6 weeks.

After thawing, the homogenate is diluted 1:10 with assay buffer (50 mM Tris, 150 mM NaCl, 5 mM MgCl$_2$, 1 mM EDTA, pH 7.40) and homogenized for 30 seconds with an Ultra-Turrax. 230 μL of the homogenized preparation are incubated for 180 minutes at ambient temperature with 50 pM $^{125}$I-iodotyrosyl-Calcitonin-Gene-Related Peptide (Amersham) and increasing concentrations of the test substances in a total volume of 250 μL. The incubation is ended by rapid filtration using a GF/B-glass fibre filter treated with polyethyleneimine (0.1%) by means of a cell harvester. The protein-bound radioactivity is determined using a gamma counter. The non-specific binding is defined as the bound radioactivity in the presence of 1 μM of human CGRP-alpha during incubation.

The concentration-binding curves are analyzed using a computer-aided nonlinear curve adaptation.

The compounds of general formula I have IC$_{50}$-values ≦10000 nM in the test described.

B. CGRP Antagonism in SK-N-MC Cells

SK-N-MC cells (1 million cells) are washed twice with 250 μL of incubation buffer (Hanks' HEPES, 1 mM 3-isobutyl-1-methylxanthine, 1% BSA, pH 7.4) and pre-incubated at 37° C. for 15 minutes. After the addition of CGRP (10 μL) as agonist in increasing concentrations ($10^{11}$ to $10^{-6}$ M), or additionally the substance in 3 to 4 different concentrations, the mixture is incubated for a further 15 minutes.

Intracellular cAMP is then extracted by the addition of 20 μL of 1M HCl and centrifugation (2000×g, 4° C. for 15 minutes). The supernatants are frozen in liquid nitrogen and stored and at −20° C.

The cAMP contents of the samples are determined by radioimmunoassay (Messrs. Amersham) and the $pA_2$ values of antagonistically acting substances are determined graphically.

The compounds of general formula I display CGRP-antagonistic properties in the in vitro test model described at doses ranging from $10^{-11}$ to $10^{-5}$ M.

On the basis of their pharmacological properties the compounds of general formula I and the salts thereof with physiologically acceptable acids or bases are thus suitable for the acute and prophylactic treatment of headaches, particularly migraine and cluster headaches. The compounds of general formula I also have a beneficial effect on the following diseases: non-insulin-dependent diabetes mellitus ("NIDDM"), cardiovascular diseases, skin diseases, particularly thermal and radiation-induced skin damage including sunburn, inflammatory diseases, e.g., inflammatory joint diseases (arthritis), inflammatory lung diseases, allergic rhinitis, asthma, diseases accompanied by excessive vasodilatation and a consequent reduction in bloodflow through the tissues, e.g., shock and sepsis, as well as morphine tolerance. In addition, the compounds of general formula I exhibit an alleviating effect on pain in general and are also suitable for fighting menopausal hot flushes.

The dosage required to achieve a corresponding effect is appropriately 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight, when administered by oral or nasal route or by inhalation, in each case 1 to 3×daily.

For this purpose the compounds of general formula I prepared according to the invention, optionally combined with other active substances such as e.g., antiemetics, prokinetics, neuroleptics, antidepressants, neurokinin antagonists, anticonvulsants, histamine-H 1-receptor antagonists, antimuscarinics, β-blockers, α-agonists and α-antagonists, ergot alkaloids, weak analgesics, non-steroidal antiphlogistics, corticosteroids, calcium antagonists, $5\text{-HT}_{1D}$-agonists, $5\text{-HT}_{1F}$-agonists or other antimigraine agents, together with one or more inert conventional carriers and/or diluents, e.g., with corn starch, lactose, glucose, microcrystalline cellulose, magnesium stearate, polyvinyl-pyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, may be made into conventional galenic preparations such as plain or coated tablets, capsules, powders, suspensions, solutions, metered aerosols or suppositories.

Thus, additional active substances for the combinations mentioned above may be for example meloxicam, ergotamine, dihydroergotamine, metoclopramide, domperidone, diphenhydramine, cyclizine, promethazine, chlorpromazine, dexamethasone, flunarizine, dextropropoxyphen, meperidine, propranolol, nadolol, atenolol, clonidine, indoramine, carbamazepine, phenytoin, valproate, amitryptiline, lidocaine, diltiazem or sumatriptan and other $5\text{-HT}_{1D}$ agonists such as, e.g., naratriptan, zolmitriptan, avitriptan, rizatriptan and eletriptan. The dosage for these active substances is usefully 1/5 of the minimum dose normally recommended up to 1/1 of the minimum dose normally recommended, i.e., for example 20 to 100 mg of sumatriptan.

The invention further relates to the use of the compounds of general formula I as valuable adjuvants for the production and purification (by affinity chromatography) of antibodies, and also, after suitable radiolabeling, for example by direct labeling with $^{125}$I or $^{131}$I or by tritiation of suitable precursors, for example by replacing halogen atoms with tritium, in RIA and ELISA assays and as diagnostic or analytical aids in neurotransmitter research.

The Examples which follow are intended to illustrate the invention:

Preliminary Remarks

Satisfactory elementary analyses, IR, UV, $^1$H-NMR and usually mass spectra have been obtained for all the compounds. Unless otherwise specified, $R_f$-values were determined using ready made silica gel TLC plates 60 $F_{254}$ (E. Merck, Darmstadt, serial no. 5729) without chamber saturation. If precise details as to configuration are not given, it is unclear whether the compounds are pure enantiomers or whether partial or total racemization has occurred. For the chromatography the following eluants or mixtures of eluants were used:

FM1=dichloromethane/cyclohexane/methanol/ammonia 7/1.5/1.5/0.2 (v/v/v/v)

FM2=dichloromethane/methanol/ammonia 7.5/2.5/0.5 (v/v/v)

FM3=dichloromethane/methanol 8/2 (v/v)

FM4=dichloromethane/ethyl acetate/methanol/cyclohexane/conc. aqueous ammonia=59/25/7.5/7.5/1 (v/v/v/v/v)

FM5=ethyl acetate/dichloromethane=7/3 (v/v)

FM6=ethyl acetate/petroleum ether=1/1 (v/v)

FM7=dichloromethane/methanol/conc. aqueous ammonia= 80/20/1 (v/v/v)

The following abbreviations are used in the description of the experiments:

mp.: melting point (D): (decomposition)

DIEA: N,N-diisopropyl-N-ethylamine

Boc: (1,1-dimethylethoxy)carbonyl

TBTU: 2-(1H-benzotriazol-1-yl)-1,1,3,3-tetramethyluronium-tetrafluoroborate

HOBt: 1-hydroxybenzotriazole-hydrate

CDT: 1,1'-carbonyldi-(1,2,4-triazole)

THF: tetrahydrofuran

DMF: dimethylformamide

Fmoc: (9-fluorenylmethoxy)carbonyl

EE: ethyl acetate

PE: petroleum ether

Sv: solvent

EXAMPLE 1

1-[4-amino-3,5-dibromo-N-[[4-(3,4-dihydro-2(1H)-oxoquinazolin-3-yl)-1-piperidinyl] methylsulfonyliminomethyl]-D-phenyl-alanyl]-4-(1-piperidinyl)-piperidine a) 1-[4-amino-3,5-dibromo-N-[(phenoxy) methylsulfonyliminomethyl]-D-phenylalanyl]-4-(1-piperidinyl)-piperidine The mixture of 0.5 g (1.716 mmol) of N-methanesulfonylimino-diphenylcarbonate, 0.72 g (1.005 mmol) of 1-(4-amino-3,5-dibromo-D-phenylalanyl)-4-(1-piperidinyl)piperidine-bis-(trifluoroacetate), 0.5 mL (3.0 mmol) of DIEA and 50 mL of dichloromethane was stirred for 1 hour at room temperature, then concentrated by evaporation in vacuo, taken up once more in 50 mL of dichloromethane, washed successively with 20 mL of 0.5 N sodium hydroxide solution and water, dried over magnesium sulfate and evaporated down in vacuo. The crude product obtained in a yield of 0.67 g (97% of theory) was used without further purification in the following step.

b) 1-[4-amino-3,5-dibromo-N-[[4-(3,4-dihydro-2(1H)-oxoquinazolin-3-yl)-1-piperidinyl]methylsulfonyliminomethyl]-D-phenylalanyl]-4-(1-piperidinyl)-piperidine The mixture of 0.4 g (0.584 mmol) of 1-[4-amino-3,5-dibromo-N-[(phenoxy)methylsulfonyliminomethyl]-D-phenylalanyl]-4-(1-piperidinyl)-piperidine, 0.46 g (1.989 mmol) of 3,4-dihydro-3-(4-piperidinyl)-2(1H)-quinazolinone and 10 mL of 2-pentanol was refluxed for 14 hours. The mixture was concentrated by evaporation in vacuo, the residue was purified by column chromatography on silica gel (MN-silica gel 60, Macherey-Nagel, 30–60 μm) using first of all dichloromethane, then methanol/conc. ammonia (9/1 v/v) as eluant. After working up in the usual way 130 mg (27% of theory) of an amorphous, colorless solid product were obtained.

IR (KBr): 1664 cm$^{-1}$ (C=O)
$R_f$: 0.53 (FM1)
ESI-MS: (M+H)$^+$=821/823/825 (Br$_2$)

EXAMPLE 2

1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-piperidinyl)-piperidine a) 1-[4-amino-3,5-dibromo-N-[(phenoxy)cyanoiminomethyl]-D-phenylalanyl]-4-(1-piperidinyl)-piperidine Prepared analogously to Example 1 a) from N-cyanoiminodiphenylcarbonate and 1-(4-amino-3,5-dibromo-D-phenylalanyl)-4-(1-piperidinyl)piperidine-bis-(trifluoroacetate) in a quantitative yield. The crude product obtained was used in the following step without further purification.

b) 1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-piperidinyl)-piperidine Prepared analogously to Example 1b) from 3,4-dihydro-3-(4-piperidinyl)-2(1H)-quinazolinone and 1-[4-amino-3,5-dibromo-N-[(phenoxy)cyanoiminomethyl]-D-phenylalanyl]-4-(1-piperidinyl)-piperidine in a yield of 43% of theory. Colorless, amorphous substance.

IR (KBr): 1664 (C=O), 2173 (CN) cm$^{-1}$
$R_f$: 0.48 (FM1)
ESI-MS: (M+H)$^+$=768/770/772 (Br$_2$)

EXAMPLE 3

1-[4-amino-3,5-dibromo-N-[[4-(3,4-dihydro-2(1H)-oxoquinazolin-3-yl)-1-piperidinyl]phenylsulfonyliminomethyl]-D-phenyl-alanyl]-4-(1-piperidinyl)-piperidine a) 1-[4-amino-3,5-dibromo-N-[(phenoxy)phenylsulfonyliminomethyl]-D-phenylalanyl]-4-(1-piperidinyl)-piperidine Prepared analogously to Example 1a) from N-benzenesulfonyl-iminodiphenylcarbonate and 1-(4-amino-3,5-dibromo-D-phenylalanyl)-4-(1-piperidinyl)piperidine-bis-(trifluoroacetate) in a yield of 60% of theory. Colorless, amorphous substance, $R_f$ 0.41 (eluant: dichloromethane/methanol/conc. ammonia 9/1/0.1).

b) 1-[4-amino-3,5-dibromo-N-[[4-(3,4-dihydro-2(1H)-oxoquinazolin-3-yl)-1-piperidinyl]phenylsulfonyliminomethyl]-D-phenylalanyl]-4-(1-piperidinyl)-piperidine Prepared analogously to Example 1b) from 3,4-dihydro-3-(4-piperidinyl)-2(1H)-quinazolinone and 1-[4-amino-3,5-dibromo-N-[(phenoxy)phenylsulfonyliminomethyl]-D-phenylalanyl]-4-(1-piperidinyl)-piperidine in a yield of 33% of theory. Colorless, amorphous substance.

IR (KBr): 1664 cm$^{-1}$ (C=O)
$R_f$: 0.50 (FM1)
ESI-MS: (M+H)$^+$=883/885/887(Br$_2$)

EXAMPLE 4

1-[3,5-dibromo-N-[[4-(3,4-dihydro-2(1H)-oxoquinazolin-3-yl)-1-piperidinyl]cyanoiminomethyl]-D-tyrosyl]-4-(1-piperidinyl)-piperidine a) 1-[3,5-dibromo-N-[(phenoxy)cyanoiminomethyl]-D-tyrosyl]-4-(1-piperidinyl)-piperidine Prepared analogously to Example 1a) from N-cyanoiminodiphenylcarbonate and 1-(3,5-dibromo-D-tyrosyl)-4-(1-piperidinyl)piperidine-bis-(trifluoroacetate) in a yield of 23% of theory. After trituration with t-butylmethylether/isopropanol (1/1 v/v): Colorless, crystalline substance.

b) 1-[3,5-dibromo-N-[[4-(3,4-dihydro-2(1H)-oxoquinazolin-3-yl)-1-piperidinyl]cyanoiminomethyl]-D-tyrosyl]-4-(1-piperidinyl)-piperidine Prepared analogously to Example 1b) from 3,4-dihydro-3-(4-piperidinyl)-2(1H)-quinazolinone and 1-[3,5-dibromo-N-[(phenoxy)cyanoiminomethyl]-D-tyrosyl]-4-(1-piperidinyl)piperidine in a yield of 20% of theory. Colorless, amorphous substance.

IR (KBr): 1658 (C=O), 2173 (CN) cm$^{-1}$
$R_f$: 0.28 (FM1)
ESI-MS: (M+H)$^+$=769/771/773(Br$_2$)

EXAMPLE 5

1-[N$^2$-[3,5-dibromo-N-[[4-(3,4-dihydro-2(1H)-oxoquinazolin-3-yl)-1-piperidinyl]methylsulfonyliminomethyl]-D-tyrosyl]-L-lysyl]-4-(4-pyridinyl)piperazine a) 1-[N$^2$-[3,5-dibromo-N-[[4-(3,4-dihydro-2(1H)-oxoquinazolin-3-yl)-1-piperidinyl]methylsulfonyliminomethyl]-D-tyrosyl]-N$^6$-(1,1-dimethylethoxycarbonyl)-L-lysyl]-4-(4-pyridinyl)piperazine To a solution of 1.0 g (1.402 mmol) of 1-[N$^2$-[3,5-dibromo-D-tyrosyl]-N$^6$-(1,1-dimethylethoxycarbonyl)-L-lysyl]-4-(4-pyridinyl)piperazine in 50 mL of dioxan was added 0.4 g (1.373 mmol) of N-(methanesulfonyl)iminodiphenylcarbonate and the mixture was stirred for 2 hours at room temperature. After the reaction was complete (TLC) 0.33 g (1.427 mmol) of 3,4-dihydro-3-(4-piperidinyl)-2(1H)-quinazolinone was added and the mixture was refluxed for 6 hours. The reaction mixture was evaporated down in vacuo, the residue remaining was purified by column chromatography on silica gel (MN-silica gel 60, Macherey-Nagel, 30–60 μm) using first of all dichloromethane, then methanol/conc. ammonia (9/1 v/v) as eluant. After working up in the usual way 590 mg (41% of theory) of an amorphous, colorless solid product were obtained.

IR (KBr): 1655 cm$^{-1}$ (C=O)
ESI-MS: (M+H)$^+$=1045/1047/1049(Br$_2$)

b) 1-[N$^2$-[3,5-dibromo-N-[[4-(3,4-dihydro-2(1H)-oxoquinazolin-3-yl)-1-piperidinyl]methylsulfonyliminomethyl]-D-tyrosyl]-L-lysyl]-4-(4-pyridinyl)piperazine To a mixture of 0.58 g (0.554 mmol)1-[N$^2$-[3,5-dibromo-N-[[4-(3,4-dihydro-2(1H)-oxoquinazolin-3-yl)-1-piperidinyl]methylsulfonyliminomethyl]-D-tyrosyl]-N$^6$-(1,1-dimethylethoxycarbonyl)-L-lysyl]-4-(4-pyridinyl)piperazine in 20 mL of methylene chloride were added 10 mL of trifluoroacetic acid. The reaction mixture was stirred for 3 hours at ambient temperature and subsequently concentrated by evaporation in vacuo. The residue remaining was taken up in 50 mL of water, and carefully made alkaline with solid sodium hydrogen carbonate. The precipitate formed was suction filtered, washed thoroughly with water and then with t-butylmethylether, and finally dried in the air. 0.36 g (69% of theory) of a colorless, amorphous solid was obtained.

IR (KBr): 1649.cm$^{-1}$ (C=O)
R$_f$: 0.07 (FM1)
ESI-MS: (M+H)$^+$=945/947/949 (Br$_2$)

EXAMPLE 6

1-[N$^2$-[3,5-dibromo-N-[[4-(3,4-dihydro-2(1H)-oxoquinazolin-3-yl)-1-piperidinyl]phenylsulfonyliminomethyl]-D-tyrosyl]-L-lysyl]-4-(4-pyridinyl)piperazine a) 1-[N$^2$-[3,5-dibromo-N-[[4-(3,4-dihydro-2(1H)-oxoquinazolin-3-yl)-1-piperidinyl]phenylsulfonyliminomethyl]-D-tyrosyl]-N$^6$-(1,1-dimethylethoxycarbonyl)-L-lysyl]-4-(4-pyridinyl)piperazine Prepared analogously to Example 5a) from N-(benzenesulfonyl)iminodiphenylcarbonate, 3,4-dihydro-3-(4-piperidinyl)-2(1H)-quinazolinone and 1-[N$^2$-(3,5-dibromo-D-tyrosyl)-N$^6$-(1,1-dimethylethoxycarbonyl)-L-lysyl]-4-(4-pyridinyl)piperazine in a yield of 43% of theory. Colorless, amorphous substance.

IR (KBr): 1657.cm$^{-1}$ (C=O)
ESI-MS: (M+H)$^+$=1107/1109/1111 (Br$_2$) (M+H+Na)$^{++}$=565/566/567 (Br$_2$)

b) 1-[N$^2$-[3,5-dibromo-N-[[4-(3,4-dihydro-2(1H)-oxoquinazolin-3-yl)-1-piperidinyl]phenylsulfonyliminomethyl]-D-tyrosyl]-4-(4-pyridinyl)piperazine Prepared analogously to Example 5b) from 1-[N$^2$-[3,5-dibromo-N-[[4-(3,4-dihydro-2(1H)-oxoquinazolin-3-yl)-1-piperidinyl]phenylsulfonyliminomethyl]-D-tyrosyl]-N$^6$-(1,1-dimethylethoxycarbonyl)-L-lysyl]-4-(4-pyridinyl)piperazine and trifluoroacetic acid in a yield of 91% of theory. Colorless, amorphous substance.

IR (KBr): 1649 (C=O) cm$^{-1}$
R$_f$: 0.13 (FM1)
ESI-MS: (M+H)$^+$=1007/1009/1111 (Br$_2$)

EXAMPLE 7

1-[4-amino-3,5-dibromo-N-[[4-(3,4-dihydro-2(1H)-oxoquinazolin-3-yl)-1-piperidinyl]cyanoiminomethyl]-D-phenylalanyl]-4-(1-methyl-4-piperidinyl)-piperidine The mixture of 0.35 g (1.469 mmol) of N-cyanoiminodiphenylcarbonate, 0.75 g (1.493 mmol) of 1-[4-amino-3,5-dibromo-D-phenylalanyl]-4-(1-methyl-4-piperidinyl)-piperidine and 30 mL of anhydrous dichloromethane was stirred for 14 hours at room temperature. The reaction mixture was freed from solvent, finally in vacuo, the residue was mixed with 0.35 g (1.513 mmol) of 3,4-dihydro-3-(4-piperidinyl)-2(1H)-quinazolinone and 20 mL of 2-pentanol and refluxed for 24 hours. The mixture was concentrated by evaporation in vacuo, the residue was purified by column chromatography on silica gel (MN-silica gel 60, Macherey-Nagel, 30–60 μm) using first of all dichloromethane, then methanol/conc. ammonia (9/1 v/v) as eluant. After working up in the usual way 700 mg (61% of theory) of an amorphous, colorless solid product were obtained.

IR (KBr): 1668 (C=O), 2173 (CN) cm$^{-1}$
R$_f$: 0.87 (eluant: dichloromethane/methanol/conc. ammonia 80/20/2 v/v/v)
ESI-MS: (M+H)$^+$=782/784/786 (Br$_2$)

EXAMPLE 8

1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-piperidinyl)-piperidine a) 1-[4-bromo-N-[(phenoxy)cyanoiminomethyl]-3,5-dimethyl-D,L-phenylalanyl]-4-(1-piperidinyl)-piperidine Prepared analogously to Example 1a), but using dioxan as solvent, from N-cyanoiminodiphenylcarbonate and 1-(4-bromo-3,5-dimethyl-D,L-phenylalanyl)-4-(1-piperidinyl)piperidine-bis-(trifluoroacetate) in a yield of 51% of theory. Colorless, amorphous substance.

b) 1-[4-bromo-N-[[4-(3,4-dihydro-2(1H)-oxoquinazolin-3-yl)-1-piperidinyl]cyanoiminomethyl]-3,5-dimethyl-D,L-phenylalanyl]-4-(1-piperidinyl)piperidine Prepared analogously to Example 1b) from 3,4-dihydro-3-(4-piperidinyl)-2(1H)-quinazolinone and 1-[4-bromo-N-[(phenoxy)cyanoiminomethyl]-3,5-dimethyl-D,L-phenylalanyl]-4-(1-piperidinyl)piperidine in a yield of 45% of theory. Colorless, amorphous substance.

IR (KBr): 1664 (C=O), 2173 (CN) cm$^{-1}$
R$_f$: 0.37 (eluant: dichloromethane/ethylacetate/cyclohexane/methanol/conc. ammonia 60/16/5/5/0.6 v/v/v/v/v)
MS: M$^+$702/704 (Br$_2$)

EXAMPLE 9

1-[3,5-dibromo-N-[[4-(3,4-dihydro-2(1H)-oxoquinazolin-3-yl)-1-piperidinyl]cyanoiminomethyl]-D-tyrosyl]-4-(4-pyridinyl)piperazine Prepared analogously to Example 1b) from 3,4-dihydro-3-(4-piperidinyl)-2(1H)-quinazolinone and 1-[3,5-dibromo-N-[(phenoxy)cyanoiminomethyl]-D-tyrosyl]-4-(4-pyridinyl)piperazine in a yield of 10% of theory. Colorless, amorphous substance.

IR (KBr): 1657 (C=O), 2171 (CN) cm$^{-1}$
R$_f$: 0.68 (eluant: methanol)
ESI-MS: (M+H)$^+$=764/766/768 (Br$_2$)

EXAMPLE 10

1-[4-amino-3,5-dibromo-N-[[4-(3,4-dihydro-2(1H)-oxoquinazolin-3-yl)-1-piperidinyl]cyanoiminomethyl]-D-phenylalanyl]-4-(4-pydinyl)piperazine Prepared analogously to Example 7 from N-cyanoiminodiphenylcarbonate, 3,4-dihydro-3-(4- piperidinyl)-2(1H)-quinazolinone and 1-[4-amino-3,5-dibromo-D-phenylalanyl]-4-(4-pyridinyl)piperazine in a yield of 43% of theory. Colorless, amorphous substance.

IR (KBr): 1660 (C=O), 2171 (CN) cm$^{-1}$ $R_f$: 0.27 (eluant: dichloromethane/methanol/conc. ammonia 9/1/0.1 v/v/v)

ESI-MS: (M+H)$^+$=763/765/767 (Br$_2$)

EXAMPLE 11

1-[3,5-dibromo-N-[[4-(3,4-dihydro-2(1H)-oxoquinazolin-3-yl)-1-piperidinyl] cyanoiminomethyl]-D-tyrosyl]-4-(1-methyl-4-piperidinyl)piperidine Prepared analogously to Example 7 from N-cyanoiminodiphenylcarbonate, 3,4-dihydro-3-(4-piperidinyl)-2(1H)-quinazolinone and 1-[3,5-dibromo-D-tyrosyl]-4-(4-pyridinyl)piperazine in a yield of 12% of theory. Colorless, amorphous substance.

IR (KBr): 2175 (CN) cm$^{-1}$ $R_f$: 0.22 (eluant dichloromethane/methanol/conc. ammonia 8/2/0.2 v/v/v)

ESI-MS: (M+H)$^+$=783/785/787 (Br$_2$)

EXAMPLE 12

1-[3,5-dibromo-N-[[4-[3,4-dihydro-2(1H)-oxoquinazolin-3-yl]-1-piperidinyl] cyanoiminomethyl]-D-tyrosyl]-4-(4-methyl-1-piperazinyl)piperidine Prepared analogously to Example 7 from N-cyanoiminodiphenylcarbonate, 3,4-dihydro-3-(4-piperidinyl)-2(1H)-quinazolinone and 1-[3,5-dibromo-D-tyrosyl]-4-(4-methyl-1-piperazinyl)-piperidine in a yield of 13% of theory. Colorless, amorphous substance.

IR (KBr): 1674 (C=O), 2173 (CN) cm$^{-1}$ $R_f$: 0.30 (eluant dichloromethane/methanol/conc. ammonia 8/2/0.2 v/v/v)

ESI-MS: (M+H)$^+$=784/786/788 (Br$_2$)

EXAMPLE 13

1-[4-bromo-N-[[4-(3,4-dihydro-2(1H)-oxoquinazolin-3-yl)-1-piperidinyl] cyanoiminomethyl]-3,5-dimethyl-D,L-phenylalanyl]-4-(1-methyl-4-piperidinyl)-piperidine Prepared analogously to Example 7 from N-cyanoiminodiphenylcarbonate, 3,4-dihydro-3-(4-piperidinyl)-2(1H)-quinazolinone and 1-[4-bromo-3,5-dimethyl-D-phenylalanyl]-4-(1-methyl-4-piperidinyl) piperidine in a yield of 44% of theory. Colorless, amorphous substance.

IR (KBr): 1666 (C=O), 2173 (CN) cm$^{-1}$ $R_f$: 0.63 (eluant: dichloromethane/cyclohexane/methanol/conc. ammonia 70/15/15/2 v/v/v/v)

MS: M$^+$716/718 (Br$_2$)

EXAMPLE 14

1-[4-amino-3,5-dibromo-N-[[4-[1,3-dihydro-4-phenyl-2(2H)-oxoimidazol-1-yl]-1-piperidinyl] cyanoiminomethyl]-D-phenylalanyl]-4-(4-methyl-1-piperazinyl)-piperidine a) 1-[4-amino-3,5-dibromo-N-[(phenoxy) cyanoiminomethyl]-D-phenylalanyl]-4-(4-methyl-1-piperazinyl)-piperidine Prepared analogously to Example 1a) from N-cyanoiminodiphenylcarbonate and 1-(4-amino-3,5-dibromo-D-phenylalanyl)-4-(4-methyl-1-piperazinyl) piperidine-bis-(trifluoroacetate) in a yield of 82% of theory. Colorless, crystalline substance, $R_f$ 0.56 (FM1).

IR (KBr): 1610 (C=O), 2195 (CN) cm$^{-1}$

ESI-MS: (M+H)$^+$=646/648/650 (Br$_2$)

b) 1-[4-amino-3,5-dibromo-N-[[4-[1,3-dihydro-4-phenyl-2 (2H)-oxoimidazol-1-yl]-1-piperidinyl]cyanoiminomethyl]-D-phenylalanyl]-4-(4-methyl-1-piperazinyl)-piperidine Prepared analogously to Example 1b) from 1,3-dihydro-1-(4-piperidinyl)-4-phenyl-2(2H)-imidazolone and 1-[4-amino-3,5-dibromo-N-[(phenoxy)cyanoiminomethyl]-D-phenylalanyl]-4-(4-methyl-1-piperazinyl)-piperidine in a yield of 19% of theory. Colorless, amorphous substance.

IR (KBr): 1699 (C=O), 2173 (CN) cm$^{-1}$ $R_f$: 0.15 (eluant: dichloromethane/methanol/conc. ammonia 9/1/0.1 v/v/v)

ESI-MS: (M+H)$^+$=796/798/800 (Br$_2$)

EXAMPLE 15

1-[4-amino-3,5-dibromo-N-[[4-(2,3,4,5-tetrahydro-2 (1H)-oxo-1,3-benzodiazepin-3-yl)-1-piperidinyl] cyanoiminomethyl]-D-phenylalanyl]-4-(4-methyl-1-piperazinyl)-piperidine Prepared analogously to Example 1b) from 3-(1-piperidinyl)-2,3,4,5-tetrahydro-1,3-benzodiazepin-2(1H)-one and 1-[4-amino-3,5-dibromo-N-[(phenoxy) cyanoiminomethyl]-D-phenylalanyl]-4-(4-methyl-1-piperazinyl)-piperidine in a yield of 5% of theory. Colorless, amorphous substance.

IR (KBr): 1653 (C=O), 2173 (CN) cm$^{-1}$ $R_f$: 0.27 (eluant: dichloromethane/methanol/conc. ammonia 9/1/0.1 v/v/v))

ESI-MS: (M+H)$^+$=797/799/801 (Br$_2$)

EXAMPLE 16

1-[4-amino-3,5-dibromo-N-[[4-(2,4-dihydro-5-phenyl-3(3H)-oxo-1,2,4-triazol-2-yl)-1-piperidinyl] cyanoiminomethyl]-D-phenylalanyl]-4-(1-piperidinyl)piperidine a) 1-[4-amino-3,5-dibromo-N-[(phenoxy) cyanoiminomethyl]-D-phenylalanyl]-4-(1-piperidinyl)-piperidine Prepared analogously to Example 1a) from N-cyanoiminodiphenylcarbonate and 1-(4-amino-3,5-dibromo-D-phenylalanyl)-4-(1-piperidinyl)piperidine in a yield of 93% of theory. Colorless, crystalline substance, $R_f$ 0.25 (eluant: dichloromethane/methanol 9/1 v/v).

IR (KBr): 1616 (C=O), 2197 (CN) cm$^{-1}$

ESI-MS: (M+H)$^+$=631/633/635 (Br$_2$)

b) 1-[4-amino-3,5-dibromo-N-[[4-(2,4-dihydro-5-phenyl-3 (3H)-oxo-1,2,4-triazol-2-yl)-1-piperidinyl] cyanoiminomethyl]-D-phenylalanyl]-4-(1-piperidinyl) piperidine Prepared analogously to Example 1b) from 2,4-dihydro-2-(4-piperidinyl)-5-phenyl-1,2,4-triazol-3(3H)-one and 1-[4-amino-3,5-dibromo-N-[(phenoxy)cyanoiminomethyl]-D-phenylalanyl]-4-(1-piperidinyl)piperidine in a yield of 31% of theory. Colorless, amorphous substance.

IR (KBr): 1695 (C=O), 2173 (CN) cm$^{-1}$ $R_f$: 0.26 (eluant: dichloromethane/methanol/conc. ammonia 9/1/0.1 v/v/v)

ESI-MS: (M+H)$^+$=781/783/785 (Br$_2$)

EXAMPLE 17

1-[4-amino-3,5-dibromo-N-[[4-(2,3,4,5-tetrahydro-2 (1H)-oxo-1.3-benzodiazepin-1,3-benzodiazepin-3-yl)-1-piperidinyl]cyanoiminomethyl]-D-phenylalanyl]-4-(1-piperidinyl)-piperidine Prepared analogously to Example 1b) from 3-(4-piperidinyl)-2,3,4,5-tetrahydro-1,3-benzodiazepin-2(1H)-one and 1-[4-amino-3,5-dibromo-N-[(phenoxy)cyanoiminomethyl]-D-phenylalanyl]-4-(1-piperidinyl)piperidine in a yield of 22% of theory. Colorless, crystalline substance.

IR (KBr): 1658 (C=O), 2171 (CN) cm$^{-1}$ $R_f$: 0.33 (eluant: dichloromethane/methanol/conc. ammonia 9/1/0.1 v/v/v)

ESI-MS: (M+H)$^+$=782/784/786 (Br$_2$)

EXAMPLE 18

1-[3,5-dibromo-N-[[4-(2,4-dihydro-5-phenyl-3(3H)-oxo-1,2,4-triazol-2-yl)-1-piperidinyl] cyanoiminomethyl]-D-tyrosyl]-4-(1-piperidinyl) piperidine a) 1-[3,5-dibromo-N-[(phenoxy)cyanoiminomethyl]-D-tyrosyl]-4-(1-piperidinyl)-piperidine Prepared analogously to Example 1a) from N-cyano-iminodiphenylcarbonate and 1-(3,5-dibromo-D-tyrosyl)-4-(1-piperidinyl)piperidine in a yield of 51% of theory. Colorless, crystalline substance.

$R_f$: 0.86 (eluant: dichloromethane/methanol/conc. ammonia 75/25/5 v/v/v).

ESI-MS: (M+H)$^+$=632/634/636 (Br$_2$) (M–H)$^-$=630/632/634 (Br$_2$)

b) 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-piperidinyl)piperidine Prepared analogously to Example 1b) from 2,4-dihydro-2-(4-piperidinyl)-5-phenyl-1,2,4-triazol-3(3H)-one and 1-[3,5-dibromo-N-[(phenoxy)cyanoiminomethyl]-D-tyrosyl]-4-(1-piperidinyl)piperidine in a yield of 32% of theory. Colorless, amorphous substance.

IR (KBr): 1695 (C=O), 2173 (CN) cm$^{-1}$ $R_f$: 0.33 (FM1)

ESI-MS: (M+H)$^+$=782/784/786 (Br$_2$)

EXAMPLE 19

1-[3,5-dibromo-N-[[4-(2,3,4,5-tetrahydro-2(1H)-oxo-1,3-benzodiazepin-3-yl)-1-piperidinyl] cyanoiminomethyl]-D-tyrosyl]-4-(1-piperidinyl)-piperidine Prepared analogously to Example 1b) from 3-(4-piperidinyl)-2,3,4,5-tetrahydro-1,3-benzodiazepin-2(1H)-one and 1-[4-3,5-dibromo-N-[(phenoxy)cyanoiminomethyl]-D-tyrosyl]-4-(1-piperidinyl)piperidine in a yield of 40% of theory. Colorless, amorphous substance.

IR (KBr): 1653 (C=O), 2171 (CN) cm$^{-1}$ $R_f$: 0.44 (FM1)

ESI-MS: (M+H)$^+$=783/785/787 (Br$_2$)

EXAMPLE 20

1-[3,5-dibromo-N-[[4-(2,4-dihydro-5-phenyl-3(3H)-oxo-1,2,4-triazol-2-yl)-1-piperidinyl] cyanoiminomethyl]-D-tyrosyl]-4-(1-methyl-4-piperidinyl)piperazine a) 1-[3,5-dibromo-N-[(phenoxy)cyanoiminomethyl]-D-tyrosyl]-4-(1-methyl-4-piperidinyl)piperazine Prepared analogously to Example 1a) from N-cyanoiminodiphenylcarbonate and 1-(3,5-dibromo-D-tyrosyl)-4-(1-methyl-4-piperidinyl)piperazine in a yield of 44% of theory. Colorless, crystalline substance.

$R_f$: 0.50 (eluant: dichloromethane/methanol/conc. ammonia 75/25/5 v/v/v).

IR (KBr): 1622 (C=O) cm$^{-1}$

ESI-MS: (M+H)$^+$=647/649/651 (Br$_2$) (M–H)$^-$=645/647/649 (Br$_2$)

b) 1-[3,5-dibromo-N-[[4-(2,4-dihydro-5-phenyl-3(3H)-oxo-1,2,4-triazol-2-yl)-1-piperidinyl]cyanoiminomethyl]-D-tyrosyl]-4-(1-methyl-4-piperidinyl)piperazine Prepared analogously to Example 1b) from 2,4-dihydro-2-(4-piperidinyl)-5-phenyl-1,2,4-triazol-3(3H)-one and 1-[3,5-dibromo-N-[(phenoxy)cyanoiminomethyl]-D-tyrosyl]-4-(1-methyl-4-piperidinyl)piperazine in a yield of 20% of theory. Colorless, amorphous substance.

IR (KBr): 1701 (C=O), 2173 (CN) cm$^{-1}$ $R_f$: 0.18 (eluant dichloromethane/methanol/conc. ammonia 8/2/0.2 v/v/v)

ESI-MS: (M+H)$^+$=797/799/801 (Br$_2$)

EXAMPLE 21

1-[3,5-dibromo-N-[[4-(2,3,4,5-tetrahydro-2(1H)-oxo-1,3-benzodiazepin-3-yl)-1-piperidinyl] cyanoiminomethyl]-D-tyrosyl]-4-(1-methyl-4-piperidinyl)piperazine Prepared analogously to Example 1b) from 3-(4-piperidinyl)-2,3,4,5-tetrahydro-1,3-benzodiazepin-2(1H)-one and 1-[3,5-dibromo-N-[(phenoxy)cyanoiminomethyl]-D-tyrosyl]-4-(1-methyl-4-piperidinyl)piperazine in a yield of 32% of theory. Colorless, amorphous substance.

IR (KBr): 1653 (C=O), 2171 (CN) cm$^{-11}$ $R_f$: 0.19 (eluant dichloromethane/methanol/conc. ammonia 8/2/0.2 v/v/v)

ESI-MS: (M+H)$^+$=798/800/802 (Br$_2$) (M–H)$^-$=796/798/800 (Br$_2$)

EXAMPLE 22

1-[4-amino-3,5-dibromo-N-[[4-(2,4-dihydro-5-phenyl-3(3H)-oxo-1,2,4-triazol-2-yl)-1-piperidinyl] cyanoiminomethyl]-D-phenylalanyl]-4-(1-methyl-4-piperidinyl)piperazine a) 1-[4-amino-3,5-dibromo-N-[(phenoxy)cyanoiminomethyl]-D-phenylalanyl]-4-(1-methyl-4-piperidinyl)piperazine Prepared analogously to Example 1a) from N-cyanoiminodiphenylcarbonate and 1-(4-amino-3,5-dibromo-D-phenylalanyl)-4-(1-methyl-4-piperidinyl)piperazine in a yield of 38% of theory. Colorless, crystalline substance.

$R_f$: 0.57 (FM1).

IR (KBr): 1689 (C=O) cm$^{-1}$

ESI-MS: (M+H)$^+$=646/648/650 (Br$_2$)

b) 1-[4-amino-3,5-dibromo-N-[[4-(2,4-dihydro-5-phenyl-3(3H)-oxo-1,2,4-triazol-2-yl)-1-piperidinyl]cyanoiminomethyl]-D-phenylalanyl]-4-(1-methyl-4-piperidinyl)piperazine Prepared analogously to Example 1b) from 2,4-dihydro-2-(4-piperidinyl)-5-phenyl-1,2,4-triazol-3(3H)-one and 1-[4-amino-3,5-dibromo-N-[(phenoxy)cyanoiminomethyl]-D-phenylalanyl]-4-(1-methyl-4-piperidinyl)piperazine in a yield of 9% of theory. Colorless, amorphous substance.

IR (KBr): 1701 (C=O), 2171 (CN) cm$^{-1}$ $R_f$: 0.33 (FM1)

ESI-MS: (M+H)⁺=796/798/800 (Br₂)

EXAMPLE 23

1-[4-amino-3,5-dibromo-N-[[4-(2,3,4,5-tetrahydro-2
(1H)-oxo-1,3-benzodiazepin-3-yl)-1-piperidinyl]
cyanoiminomethyl]-D-phenylalanyl]-4-(1-methyl-4-
piperidinyl)piperazine Prepared analogously to Example 1b) from 3-(4-piperidinyl)-2,3,4,5-tetrahydro-1,3-benzodiazepin-2(1H)-one and 1-[4-amino-3,5-dibromo-N-[(phenoxy)cyanoiminomethyl]-D-phenylalanyl]-4-(1-methyl-4-piperidinyl)piperazine in a yield of 15% of theory. Colorless, amorphous substance.

IR (KBr): 2173 (CN) cm⁻¹

R_f: 0.19 (FM1)

ESI-MS: (M+H)⁺=797/799/801 (Br₂)

EXAMPLE 24

1-[3,5-dibromo-N-[[4-(3,4-dihydro-2(1H)-
oxoquinazolin-3-yl)-1-piperidinyl]
cyanoiminomethyl]-4-methyl-D,L-phenylalanyl]-4-
(1-methyl-4-piperidinyl)-piperidine Prepared analogously to Example 7 from N-cyanoiminodiphenylcarbonate, 3,4-dihydro-3-(4-piperidinyl)-2(1H)-quinazolinone and 1-[3,5-dibromo-4-methyl-D,L-phenylalanyl]-4-(1-methyl-4-piperidinyl)-piperidine in a yield of 49% of theory. Colorless, crystalline substance.

IR (KBr): 1668 (C=O), 2175 (CN) cm⁻¹

R_f: 0.5 (FM1)

ESI-MS: (M+H)⁺=781/783/785 (Br₂) (M–H)⁻=779/781/783 (Br₂)

EXAMPLE 25

1-[3,5-dibromo-N-[[4-(3,4-dihydro-2(1H)-
oxoquinazolin-3-yl)-1-piperidinyl]
cyanoiminomethyl]-4-methyl-D,L-phenylalanyl]-4-
(1-piperidinyl)piperidine Prepared analogously to Example 7 from N-cyanoiminodiphenylcarbonate, 3,4-dihydro-3-(4-piperidinyl)-2(1H)-quinazolinone and 1-[3,5-dibromo-4-methyl-D,L-phenylalanyl]-4-(1-piperidinyl)piperidine in a yield of 34% of theory. Colorless, crystalline substance.

IR (KBr): 1664 (C=O), 2175 (CN) cm⁻¹

R_f: 0.55 (FM1)

ESI-MS: (M+H)⁺=767/769/771 (Br₂) (M–H)⁻=765/767/769 (Br₂)

EXAMPLE 26

1-[3,5-dibromo-N-[[4-(3,4-dihydro-2(1H)-
oxoquinazolin-3-yl)-1-piperidinyl]
cyanoiminomethyl]-4-methyl-D,L-phenylalanyl]-4-
(4-pyridinyl)piperazine Prepared analogously to Example 7 from N-cyanoiminodiphenylcarbonate, 3,4-dihydro-3-(4-piperidinyl)-2(1H)-quinazolinone and 1-[3,5-dibromo-4-methyl-D,L-phenylalanyl]-4-(4-pyridinyl)piperazine in a yield of 6% of theory. Colorless, crystalline substance.

IR (KBr): 2171 (CN) cm⁻¹

R_f: 0.60 (FM1)

ESI-MS: (M+H)⁺=762/764/766 (Br₂)

EXAMPLE 27

1-[4-amino-3,5-dibromo-N-[[4-[1,3-dihydro-2(2H)-
oxoimidazo-[4,5-c]quinolin-3-yl]-1-piperidinyl]
cyanoiminomethyl]-D-phenylalanyl]-4-(1-
piperidinyl)piperidine Prepared analogously to Example 1b) from 1,3-dihydro-3-(4-piperidinyl)-imidazo[4,5-c]quinolin-2(2H)-one and 1-[4-amino-3,5-dibromo-N-[(phenoxy)cyanoiminomethyl]-D-phenylalanyl]-4-(1-piperidinyl)piperidine in a yield of 9% of theory. Colorless, amorphous substance.

IR (KBr): 1712 (C=O), 2173 (CN) cm⁻¹

R_f: 0.45 (FM1)

ESI-MS: (M+H)⁺=805/807/809 (Br₂)

EXAMPLE 28

1-[4-amino-3,5-dibromo-N-[[4-(7-methoxy-2,3,4,5-
tetrahydro-2(1H)-oxo-1,3-benzodiazepin-3-yl)-1-
piperidinyl]cyanoiminomethyl]-D-phenylalanyl]-4-
(1-piperidinyl)-piperidine Prepared analogously to Example 1b) from 7-methoxy-3-(4-piperidinyl)-2,3,4,5-tetrahydro-1,3-benzodiazepin-2(1H)-one and 1-[4-amino-3,5-dibromo-N-[(phenoxy)cyanoiminomethyl]-D-phenylalanyl]-4-(1-piperidinyl)piperidine in a yield of 51% of theory. Colorless crystals (from acetone).

IR (KBr): 1658 (C=O), 2173 (CN) cm⁻¹

R_f: 0.65 (FM1)

ESI-MS: (M+H)⁺=812/814/816 (Br₂)

EXAMPLE 29

1-[4-amino-3,5-dibromo-N-[[4-(5,7-dihydro-6-
oxodibenzo[d,f][1,3]diazepin-5-yl)-1-piperidinyl]
cyanoiminomethyl]-D-phenylalanyl]-4-(1-
piperidinyl)-piperidine 2-nitro-2'-[[1-(phenylmethyl)-4-piperidinyl]amino]-biphenyl To a solution of 30.0 g (0.140 mol) of 2-amino-2'-nitrobiphenyl and 111.5 g (0.630 mol) of 1-(phenylmethyl)-4-piperidone in 1200 mL of dichloromethane were added a total of 140.5 g (0.630 mol) of sodium triacetoxyborohydride in batches whilst maintaining a reaction temperature of 0° C. and the mixture was then stirred for 14 hours at room temperature. It was made alkaline with sodium hydroxide solution, the dichloromethane phase was separated off, dried over sodium sulfate and concentrated by evaporation. The residue was digested with methanol, then filtered. The filtrate was evaporated down, the residue remaining was purified by chromatography on aluminium oxide (activity stage 3) using PE/EE 9/1 (v/v) as eluant. Corresponding fractions were combined, freed from solvent and used in the next step without further purification. Yield: 40.0 g (74% of theory).

2-amino-2'-[[1-(phenylmethyl)-4-piperidinyl]amino]-biphenyl

The solution of 40.0 g (0.103 mol) of 2-nitro-2'-[[1-(phenylmethyl)-4-piperidinyl]amino]-biphenyl in 500 mL of methanol was hydrogenated in the presence of 5% water-moistened rhodium on charcoal for 2 hours. The catalyst was filtered off, the solution obtained was evaporated down and the crude product thus obtained was used in the next step without further purification. Yield: 36.0 g (98% of theory).

c) 5,7-dihydro-5-[1-(phenylmethyl)-4-piperidinyl]-dibenzo[d,f][1,3]diazepin-6-one To a solution of 36.0 g (0.101 mol) of 2-amino-2'-[[1-(phenylmethyl)-4-piperidinyl]amino]-biphenyl in 200 mL of dimethylformamide were added 40.5 g (0.250 mol) of N,N'-carbonyldiimidazole, then the mixture was stirred for 2 hours at 100° C., after which the solvent was eliminated in vacuo. The residue was stirred with water, then extracted exhaustively with dichloromethane. The combined organic extracts were dried over sodium sulfate, clarified with active charcoal and evaporated down. The residue (60 g) was purified by chromatography on aluminium oxide of activity stage 3 using PE/EE 2/1 (v/v). The desired compound was obtained from the corresponding fractions in a yield of 6.2 g (16% of theory).

IR (KBr): 1676 (C=O) cm$^{-1}$
$R_f$: 0.35 (eluant: dichloromethane/methanol 9.5/0.5 v/v)
MS: M$^+$=383 d) 5,7-dihydro-5-(4-piperidinyl)-dibenzo[d,f][1,3]diazepin-6-one

The solution of 6.0 g (0.016 mol) of 5,7-dihydro-5-[1-(phenylmethyl)-4-piperidinyl]-dibenzo[d,f][1,3]diazepin-6-one in 200 mL of methanol was hydrogenated at 50° C. in the presence of 1.5 g of 10% palladium/charcoal until the uptake of hydrogen ended.

After elimination of the catalyst and solvent 3,5 g (76% of theory) of the desired compound were obtained, which was used in the next step without further purification.

IR (KBr): 1678 (C=O) cm$^{-1}$
$R_f$: 0.15 (FM1)
MS: M$^+$=293 e) 1-[4-amino-3,5-dibromo-N-[[4-(5,7-dihydro-6-oxodibenzo[d,f][1,3]diazepin-5-yl)-1-piperidinyl]cyanoiminomethyl]-D-phenylalanyl]-4-(1-piperidinyl)-piperidine Prepared analogously to Example 1b) from 5,7-dihydro-5-(4-piperidinyl)-dibenzo[d,f][1,3]diazepin-6-one and 1-[4-amino-3,5-dibromo-N-[(phenoxy)cyanoiminomethyl]-D-phenylalanyl]-4-(1-piperidinyl)piperidine in a yield of 25% of theory. Colorless crystals.

IR (KBr): 1684 (C=O), 2173 (CN) cm$^{-1}$
$R_f$: 0.65 (FM1)
ESI-MS: (M+H)$^+$=830/832/834 (Br$_2$)

EXAMPLE 30

1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(1-methyl-4-piperidinyl)piperazine Prepared analogously to Example 1b) from 7-methoxy-3-(4-piperidinyl)-2,3,4,5-tetrahydro-1,3-benzodiazepin-2(1H)-one and 1-[4-amino-3,5-dibromo-N-[(phenoxy)cyanoiminomethyl]-D-phenylalanyl]-4-(1-methyl-4-piperidinyl)piperazine in a yield of 53% of theory. Colorless crystals (diisopropylether).

IR (KBr): 1647 (C=O) cm$^{-1}$
$R_f$: 0.75 (eluant: dichloromethane/methanol/conc. ammonia 70/25/5 v/v/v)
ESI-MS: (M+H)$^+$=827/829/831 (Br$_2$) (M−H)$^-$=825/827/829 (Br$_2$)

EXAMPLE 31

1-[4-amino-3,5-dibromo-N-[[4-[1,3-dihydro-2(2H)-oxoimidazo[4,5-c]quinolin-3yl]-1-piperidinyl]cyanoiminomethyl]-D-phenylalanyl]-4-(1-methyl-4-piperidinyl)piperazine Prepared analogously to Example 1b) from 1,3-dihydro-3-(4-piperidinyl)-imidazo[4,5-c]quinolin-2(2H)-one and 1-[4-amino-3,5-dibromo-N-[(phenoxy)cyanoiminomethyl]-D-phenylalanyl]-4-(1-methyl-4-piperidinyl)piperazine in a yield of 13% of theory. Colorless, crystalline substance.

IR (KBr): 1711 (C=O) cm$^{-1}$
$R_f$: 0.70 (eluant: dichloromethane/methanol/conc. ammonia 70/25/5 v/v/v)
ESI-MS: (M+H)$^+$=820/822/824 (Br$_2$) (M−H)$^-$=818/820/822 (Br2)

EXAMPLE 32

1-[4-amino-3,5-dibromo-N-[[4-(2,3,4,5-tetrahydro-2(1H)-oxo-1,3-benzodiazepin-3-yl)-1-piperidinyl]sulfonyl]-D-phenylalanyl]-4-(1-methyl-4-piperidinyl)piperazine a) 1-[4-amino-3,5-dibromo-N-(2-hydroxyphenoxysulfonyl)-D-phenylalanyl]-4-(1-methyl-4-piperidinyl)piperazine Whilst cooling externally with ice 1.377 g (7.998 mmol) of pyrocatechol sulfate was added to a solution of 2.000 g (3.974 mmol) of 1-(4-amino-3,5-dibromo-D-phenylalanyl)-4-(1-methyl-4-piperidinyl)piperazine and 0.61 mL (0.004 mmol) of triethylamine in 50 mL of dimethylformamide and the mixture was then stirred for 1 hour whilst still being cooled with ice and for 2 hours at room temperature. The reaction mixture was concentrated by evaporation in vacuo at a maximum bath temperature of +40° C., the residue was triturated with diethylether, dried in air and used in the next step without further purification. Yield: 2.68 g (100% of theory).

$R_f$: 0.30 (FM1).

b) 1-[4-amino-3,5-dibromo-N-[[4-(2,3,4,5-tetrahydro-2(1H)-oxo-1,3-benzodiazepin-3-yl)-1-piperidinyl]sulfonyl]-D-phenylalanyl]-4-(1-methyl-4-piperidinyl)piperazine The mixture of 2.680 g (3.968 mmol) of 1-[4-amino-3,5-dibromo-N-(2-hydroxyphenoxysulfonyl)-D-phenylalanyl]-4-(1-methyl-4-piperidinyl)piperazine, 1.472 g (6.00 mmol) of 3-(4-piperidinyl)-2,3,4,5-tetrahydro-1,3-benzodiazepin-2(1H)-one and 100 mL of dioxan was refluxed for 1 hour, then evaporated down in vacuo, and the residue was stirred into 200 mL of 10% aqueous ammonia solution. The mixture thus obtained was exhaustively extracted with ethyl acetate. The combined organic extracts were dried over sodium sulfate and freed from solvent. The residue was purified by chromatography on silica gel (MN-silica gel 60, Macherey-Nagel, 30–60 μm) using FM1 as eluant. The appropriate fractions were combined, evaporated down, the residue was triturated with diethylether, suction filtered and dried in vacuo. 0.1 g (3.1% of theory) of the desired compound was obtained in the form of colorless crystals.

$R_f$: 0.65 (FM1).
IR (KBr): 1657 (C=O) cm$^{-1}$
ESI-MS: (M+H)$^+$=809/811/813 (Br$_2$)

EXAMPLE 33

1-[3,5-dibromo-N-[[4-(7-methoxy-2,3,4,5-tetrahydro-2(1H)-oxo-1,3-benzodiazepin-3-yl)-1-piperidinyl]cyanoiminomethyl]-D-tyrosyl]-4-(1-piperidinyl)-piperidine Prepared analogously to Example 1b) from 7-methoxy-3-(4-piperidinyl)-2,3,4,5-tetrahydro-1,3-benzodiazepin-2(1H)-one and 1-[3,5-dibromo-N-[(phenoxy)cyanoiminomethyl]-D-tyrosyl]-4-(1-piperidinyl)piperidine in a yield of 24% of theory. Colorless crystals (diethylether).

IR (KBr): 1653 (C=O) cm$^{-1}$ $R_f$: 0.31 (FM1)
ESI-MS: (M+H)⁺=813/815/817 (Br₂)

EXAMPLE 34

1-[3,5-dibromo-N-[[4-(7-methoxy-2,3,4,5-tetrahydro-2(1H)-oxo-1,3-benzodiazepin-3-yl)-1 piperidinyl]cyanoiminomethyl]-D-tyrosyl]-4-(1-methyl-4-piperidinyl)piperazine Prepared analogously to Example 1b) from 7-methoxy-3-(4-piperidinyl)-2,3,4,5-tetrahydro-1,3-benzodiazepin-2(1H)-one and 1-[3,5-dibromo-N-[(phenoxy)cyanoiminomethyl]-D-tyrosyl]-4-(1-methyl-4-piperidinyl)piperazine in a yield of 23% of theory. Colorless crystals (diethylether).

IR (KBr): 1647 (C=O) cm⁻¹
$R_f$: 0.42 (eluant: dichloromethane/methanol/conc. ammonia 75/25/5 v/v/v)
ESI-MS: (M−H)⁻=826/828/830 (Br₂)

EXAMPLE 35

1-[3,5-dibromo-N-[[4-[1,3-dihydro-2(2H)-oxoimidazo[4,5-c]-quinolin-3-yl]-1-2piperidinyl] cyanoiminomethyl]-D-tyrosyl]-4-(1-piperidinyl)piperidine Prepared analogously to Example 1b) from 1,3-dihydro-3-(4-piperidinyl)-imidazo[4,5-c]quinolin-2(2H)-one and 1-[3,5-dibromo-N-[(phenoxy)cyanoiminomethyl]-D-tyrosyl]-4-(1-piperidinyl)piperidine in a yield of 10% of theory. Colorless, crystalline substance.

IR (KBr): 1709 (C=O) cm⁻¹
$R_f$: 0.21 (FM1)
ESI-MS: (M+H)⁺=806/808/810 (Br₂) (M−H)⁻=804/806/808 (Br2)

EXAMPLE 36

1-[3,5-dibromo-N-[[4-[1,3-dihydro-2(2H)-oxoimidazo[4,5-c]-quinolin-3-yl]-1- piperidinyl] cyanoiminomethyl]-D-tyrosyl]-4-(1-methyl-4-piperidinyl)piperazine Prepared analogously to Example 1b) from 1,3-dihydro-3-(4-piperidinyl)imidazo[4,5-c]quinolin-2(2H)-one and 1-[3,5-dibromo-N-[(phenoxy)cyanoiminomethyl]-D-tyrosyl]-4-(1-methyl-4-piperidinyl)piperazine in a yield of 31% of theory. Colorless, crystalline substance.

IR (KBr): 1635, 1705 (C=O) cm⁻¹
$R_f$: 0.07 (eluant: dichloromethane/methanol/conc. ammonia 80/20/2 v/v/v)
ESI-MS: (M+H)⁺=821/823/825 (Br₂) (M−H)⁻=819/821/823 (Br₂)

EXAMPLE 37

1-[4-amino-3,5-dibromo-N-[[4-(7-methoxy-2,3,4,5-tetrahydro-2(1H)-oxo-1,3-benzodiazepin-3-yl)-1-piperidinyl]cyanoiminomethyl]-D-phenylalanyl]-4-(4-methyl-1-piperazinyl)-piperidine Prepared analogously to Example 1b) from 7-methoxy-3-(4-piperidinyl)-2,3,4,5-tetrahydro-1,3-benzodiazepin-2(1H)-one and 1-[4-amino-3,5-dibromo-N-[(phenoxy)cyanoiminomethyl]-D-phenylalanyl]-4-(4-methyl-1-piperazinyl)piperidine in a yield of 21% of theory. Colorless crystals (diethylether).

$R_f$: 0.53 (eluant: dichloromethane/methanol/conc. ammonia 80/20/2 v/v/v)
ESI-MS: (M+H)⁺=827/829/831 (Br₂) (M−H)⁻=825/827/829 (Br₂) (M+Na)⁺=849/851/853 (Br₂)

EXAMPLE 38

1-[4-amino-3,5-dibromo-N-[[4-[1,3-dihydro-2(2H)-oxoimidazo[4,5-c]quinolin-3-yl]-1-piperidinyl] cyanoiminomethyl]-D-phenylalanyl]-4-(4-methyl 1-piperazinyl)piperidine Prepared analogously to Example 1b) from 1,3-dihydro-3-(4-piperidinyl)-imidazo[4,5-c]quinolin-2(2H)-one and 1-[4-amino-3,5-dibromo-N-[(phenoxy)cyanoiminomethyl]-D-phenylalanyl]-4-(4-methyl-1-piperazinyl)piperidine in a yield of 8% of theory. Colorless, crystalline substance (diisopropylether).

IR (KBr): 1714 (C=O) cm⁻¹
$R_f$: 0.43 (eluant: dichloromethane/methanol/conc. ammonia 80/20/2 v/v/v)
ESI-MS: (M+H)⁺=820/822/824 (Br₂) (M−H)⁻=818/820/822 (Br₂)

The Examples which follow describe the preparation of pharmaceutical formulations which contain as active substance any compound of general formula I:

EXAMPLE I

Capsules for Inhalation of a Powder Containing 1 mg of Active Substance

| Composition: 1 capsule for powder inhalation contains: | |
|---|---|
| active substance | 1.0 mg |
| lactose | 20.0 mg |
| hard gelatine capsules | 50.0 mg |
| | 71.0 mg |

Method of Preparation

The active substance is ground to the required particle size for inhalation. The ground active substance is homogeneously mixed with the lactose. The mixture is packed into hard gelatine capsules.

EXAMPLE II

Solution for Respimat® Inhalation Containing 1 mg of Active Substance Composition

| Composition: 1 actuation contains: | |
|---|---|
| active substance | 1.0 mg |
| benzalkonium chloride | 0.002 mg |
| disodium edetate | 0.0075 mg |
| purified water ad | 15.0 μL |

Method of Preparation

The active substance and benzalkonium chloride are dissolved in water and transferred into Respimat® cartridges.

EXAMPLE III

Solution for Inhalation with a Nebulizer Containing 1 mg of Active Substance Composition

| Composition: 1 vial contains: | |
|---|---|
| active substance | 0.1 g |
| sodium chloride | 0.18 g |
| benzalkonium chloride | 0.002 g |
| purified water ad | 20.0 mL |

Method of Preparation

The active substance, sodium chloride and benzalkonium chloride are dissolved in water.

EXAMPLE IV

Propellant Gas-operated Metering Aerosol Containing 1 mg of Active Substance Composition

| Composition: 1 puff contains: | |
|---|---|
| active substance | 1.0 mg |
| lecithin | 0.1% |
| propellant gas ad | 50.0 µL |

Method of Preparation

The micronized active substance is homogeneously suspended in the mixture of lecithin and propellant gas. The suspension is transferred into a pressurized container with a metering valve.

EXAMPLE V

| Composition: | |
|---|---|
| active substance | 1.0 mg |
| sodium chloride | 0.9 mg |
| benzalkonium chloride | 0.025 mg |
| disodium edetate | 0.05 mg |
| purified water ad | 0.1 mL |

Method of Preparation

The active substance and the excipients are dissolved in water and transferred into a suitable container.

EXAMPLE VI

Injectable Solution Containing 5 mg of Active Substance per 5 mL

| Composition: | |
|---|---|
| active substance | 5 mg |
| glucose | 250 mg |
| human serum albumin | 10 mg |
| glycofurol | 250 mg |
| water for injections ad | 5 mL |

Preparation

Glycofurol and glucose are dissolved in water for injections (WfI); human serum albumin is added; active substance is dissolved with heating; solution topped up with WfI to the specified volume; transferred into ampoules under nitrogen gas.

EXAMPLE VII

Injectable Solution Containing 100 mg Active Substance per 20 mL

| Composition: | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 mL |

Preparation

The Polysorbate 80, sodium chloride, monopotassium dihydrogen phosphate and disodium hydrogen phosphate are dissolved in water for injections (WfI); human serum albumin is added; active substance is dissolved with heating; solution topped up to the specified volume with WfI; transferred into ampoules.

EXAMPLE VIII

Freeze-dried Preparation Containing 10 mg of Active Substance

| Composition: | |
|---|---|
| active substance | 10 mg |
| mannitol | 300 mg |
| human serum albumin | 20 mg |

Preparation

Mannitol is dissolved in water for injections (WfI); human serum albumin is added; active substance is dissolved with heating; solution topped up to the specified volume with WfI; transferred into vials; freeze-dried.

| Solvent for freeze-dried preparation: | |
|---|---|
| Polysorbate 80 = Tween 80 | 20 mg |
| mannitol | 200 mg |
| water for injections ad | 10 mL |

Preparation

Polysorbate 80 and mannitol are dissolved in water for injections (WfI); transferred into ampoules.

EXAMPLE IX

| Composition: | |
|---|---|
| active substance | 20 mg |
| lactose | 120 mg |
| corn starch | 40 mg |
| magnesium stearate | 2 mg |
| Povidone K 25 | 18 mg |

Preparation

The active substance, lactose and corn starch are homogeneously mixed; granulated with an aqueous solution of Povidone; mixed with magnesium stearate; compressed in a tablet press; weight of tablet 200 mg.

EXAMPLE X
Capsules Containing 20 mg of Active Substance

| Composition: | |
|---|---|
| active substance | 20 mg |
| corn starch | 80 mg |
| highly dispersed silica | 5 mg |
| magnesium stearate | 2.5 mg |

Preparation

The active substance, corn starch and silica are homogeneously mixed; mixed with magnesium stearate; the mixture is packed into size 3 hard gelatine capsules in a capsule filling machine.

EXAMPLE XI
Suppositories Containing 50 mg of Active Substance

| Composition: | |
|---|---|
| active substance | 50 mg |
| hard fat (Adeps solidus) q.s. ad | 1700 mg |

Preparation

The hard fat is melted at about 38° C.; the ground active substance is homogeneously dispersed in the molten fat; after cooling to about 35° C. it is poured into chilled moulds.

EXAMPLE XII
Aqueous Solution for Nasal Use Containing 10 mg of Active Substance

| Composition: | |
|---|---|
| active substance | 10.0 mg |
| sufficient hydrochloric acid to form a neutral salt | |
| methyl parahydroxybenzoate (PHB) | 0.01 mg |
| propyl parahydroxybenzoate (PHB) | 0.005 mg |
| purified water ad | 1.0 mL |

Preparation

The active substance is dissolved in purified water; hydrochloric acid is added until the solution becomes clear; methyl and propyl PHB are added; the solution is topped up to the specified volume with purified water; the solution is sterile filtered and transferred into a suitable container.

EXAMPLE XIII

| Composition: | |
|---|---|
| active substance | 5 mg |
| 1,2-propanediol | 300 mg |
| hydroxyethylcellulose | 5 mg |
| sorbic acid | 1 mg |
| purified water ad | 1 mL |

Preparation

The active substance is dissolved in 1,2-propanediol; a hydroxyethyl-cellulose solution in purified water containing sorbic acid is prepared and added to the solution of the active substance; the solution is sterile filtered and transferred into a suitable container.

EXAMPLE XIV
Aqueous Solution for Intravenous Administration Containing 5 mg of Active Substance

| Composition: | |
|---|---|
| active substance | 5 mg |
| 1,2-propanediol | 300 mg |
| mannitol | 50 mg |
| water for injections (WfI) ad | 1 mL |

Preparation

The active substance is dissolved in 1,2-propanediol; the solution is made up to roughly the specified volume with WfI; the mannitol is added and made up to the specified volume with WfI; the solution is sterile filtered, transferred into individual containers and autoclaved.

EXAMPLE XV
Liposomal Formulation for Intravenous Injection Containing 7.5 mg of Active Substance

| Composition: | |
|---|---|
| active substance | 7.5 mg |
| egg lecithin, e.g., Lipoid E 80 | 100.0 mg |
| cholesterol | 50.0 mg |
| glycerol | 50.0 mg |
| water for injections ad | 1.0 mL |

Preparation

The active substance is dissolved in a mixture of lecithin and cholesterol; the solution is added to a mixture of glycerol and WfI and homogenized by high pressure homogenisation or by Microfluidizer technology; the liposomal formulation thus obtained is transferred into a suitable container under aseptic conditions.

EXAMPLE XVI
Suspension for Nasal Administration Containing 20 mg of Active Substance

| Composition: | |
|---|---|
| active substance | 20.0 mg |
| carboxymethylcellulose (CMC) | 20.0 mg |
| sodium monohydrogen phosphate/sodium dihydrogen phosphate buffer pH | 6.8 q.s. |
| sodium chloride | 8.0 mg |
| methyl parahydroxybenzoate | 0.01 mg |
| propyl parahydroxybenzoate | 0.003 mg |
| purified water ad | 1.0 mL |

Preparation

The active substance is suspended in an aqueous CMC solution; the other ingredients are added successively to the suspension and the suspension is made up to the specified volume with purified water.

EXAMPLE XVII
Aqueous Solution for Subcutaneous Administration Containing 10 mg of Active Substance

| Composition: | |
|---|---|
| active substance | 10.0 mg |
| sodium monohydrogen phosphate/sodium dihydrogen phosphate buffer | q.s. ad pH 7.0 |
| sodium chloride | 4.0 mg |
| water for injections ad | 0.5 mL |

Preparation

The active substance is dissolved in the phosphate buffer solution, after the addition of the common salt the solution is made up to the specified volume with water. The solution is sterile filtered, transferred into a suitable container and autoclaved.

EXAMPLE XVIII
Aqueous Suspension for Subcutaneous Administration Containing 5 mg of Active

| Composition: | |
|---|---|
| active substance | 5.0 mg |
| Polysorbate 80 | 0.5 mg |
| water for injections | 0.5 mL |

Preparation

The active substance is suspended in the Polysorbate 80 solution and comminuted to a particle size of about 1 μm using a suitable dispersing method (e.g., wet grinding, high pressure homogenisation, microfluidisation etc.). The suspension is transferred into a suitable container under aseptic conditions.

What is claimed is:

1. A compound of the formula

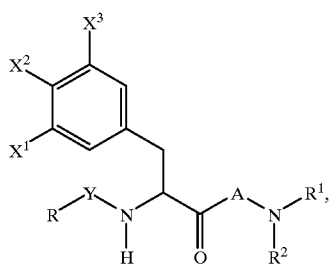

(I)

R is a 1-piperidinyl group substituted in the 4 position by a mono- or di-unsaturated 5- to 7-membered aza, diaza, or triaza heterocyclic group bound via a nitrogen atom, which contains one or two carbonyl groups linked to a nitrogen atom,
   wherein the mono- or di-unsaturated 5- to 7-membered aza, diaza, or triaza heterocyclic groups of R are optionally substituted at a carbon atom by an optionally substituted phenyl group,
   wherein an olefinic double bond of one of the mono- or di-unsaturated 5- to 7-membered aza, diaza, or triaza heterocyclic groups of R is optionally condensed with a benzene, pyridine, diazine, 1,3-oxazole, thiophene, furan, thiazole, pyrrole, N-methylpyrrole, quinoline, imidazole, or N-methylimidazole ring or two olefinic double bonds in one of the di-unsaturated 5- to 7-membered aza, diaza, or triaza heterocyclic groups of R are optionally benzocondensed, and
   wherein the phenyl group optionally attached to the mono- or di-unsaturated 5- to 7-membered aza, diaza, or triaza heterocyclic groups of R and the benzo-, thieno-, pyrido-, and diazino-condensed heterocyclic groups of R are optionally, additionally mono-, di-, or trisubstituted in the carbon skeleton by fluorine, chlorine, or bromine atoms, by alkyl groups, cycloalkyl groups with 3 to 8 carbon atoms, nitro, alkoxy, alkylthio, alkylsulphinyl, alkylsulphonyl, alkylsulphonylamino, phenyl, phenylalkoxy, trifluoromethyl, alkoxycarbonyl, alkoxycarbonylalkyl, carboxy, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, hydroxyalkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, aminocarbonylaminoalkyl, alkylaminocarbonylamino, alkanoyl, cyano, trifluoromethoxy, trifluoromethylthio, trifluoromethylsulphinyl, or trifluoromethylsulphonyl groups, wherein the substituents are identical or different;

Y is a divalent group selected from

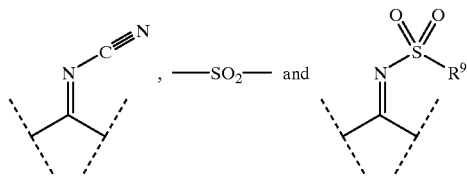

wherein $R^9$ is an alkyl group with 1 to 4 carbon atoms or a phenyl group optionally substituted by a halogen atom or a methyl or methoxy group;

$X^1$, $X^2$ and $X^3$, which are identical or different, are a hydrogen atom, a fluorine, chlorine, or bromine atom, a branched or unbranched alkyl group, an alkoxy, trifluoromethyl, dialkylaminoalkyl, dialkylaminoalkoxy, nitro, hydroxy, amino, acetylamino, methylsulphonyloxy, aminocarbonyl, alkylaminocarbonyl, dialkylaminocarbonyl, alkanoyl, cyano, trifluoromethoxy, trifluoromethylthio, trifluoromethylsulphinyl, or trifluoromethylsulphonyl group;

A is a bond or the divalent group

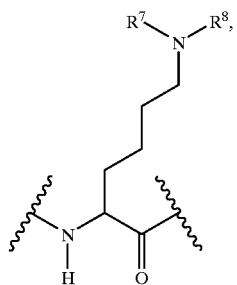

(II)

linked via the —CO group to the NR¹R² group of formula I, wherein $R^7$ is a hydrogen atom or a methyl group, $R^8$ is a hydrogen atom, or a methyl, methoxycarbonyl, ethoxycarbonyl, n-propoxycarbonyl, isopropoxycarbonyl, tert-butoxycarbonyl, or acetyl group;

$R^1$ is a hydrogen atom,
an alkyl group with 1 to 7 carbon atoms, which is optionally substituted in the ω position by a cyclohexyl, phenyl, pyridinyl, diazinyl, hydroxy, amino, alkylamino, dialkylamino, carboxy, aminocarbonyl, aminocarbonylamino, acetylamino, 1-pyrrolidinyl, 1-piperidinyl, 4-(1-piperidinyl)-1-piperidinyl, 4-morpholinyl, hexahydro-1H-1-azepinyl, [bis-(2-hydroxyethyl)]amino, 4-alkyl-1-piperazinyl, or 4-(ω-hydroxyalkyl)-1-piperazinyl group,
a phenyl or pyridinyl group,
wherein the heterocyclic groups and phenyl groups of $R^1$ are optionally, additionally mono-, di-, or trisubstituted in the carbon skeleton by fluorine, chlorine, or bromine atoms, by methyl, alkoxy, trifluoromethyl, hydroxy, amino, acetylamino, aminocarbonyl, cyano, methylsulphonyloxy, trifluoromethoxy, trifluoromethylthio, trifluoromethylsulphinyl, or trifluoromethylsulphonyl groups, wherein the substituents are identical or different, $R^2$ is a hydrogen atom or an alkyl group with 1 to 3 carbon atoms optionally substituted by a phenyl or pyridinyl group, or $R^1$ and $R^2$ together with the included nitrogen atom are a group of general formula III

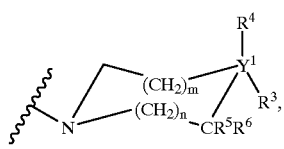

(III)

$Y^1$ is a carbon atom or, if $R^4$ is a free pair of electrons, a nitrogen atom, m is the number 0, 1, or 2, n is the number 0, 1, or 2, $R^3$ is a hydrogen atom, or an amino, alkylamino, dialkylamino, alkyl, cycloalkyl, aminoalkyl, alkylaminoalkyl, dialkylaminoalkyl, aminoiminomethyl, aminocarbonylamino, alkylaminocarbonylamino, cycloalkylaminocarbonylamino, phenylaminocarbonylamino, aminocarbonylalkyl, aminocarbonylaminoalkyl, alkoxycarbonyl, alkoxycarbonylalkyl, carboxyalkyl, or carboxy group, a phenyl, pyridinyl, diazinyl, 1-naphthyl, 2-naphthyl, pyridinylcarbonyl, or phenylcarbonyl group, each of which is optionally mono-, di-, or trisubstituted in the carbon skeleton by fluorine, chlorine, or bromine atoms, by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino)alkanoyl, ω-(dialkylamino)alkyl, ω-(dialkylamino)hydroxyalkyl, ω-(carboxy)alkanoyl, trifluoromethoxy, trifluoromethylthio, trifluoromethylsulphinyl, or trifluoromethylsulphonyl groups, wherein the optional substituents are identical or different, a 4- to 10-membered azacycloalkyl group, a 5- to 10-membered oxaza, thiaza, or diazacycloalkyl group, or a 6- to 10-membered azabicycloalkyl group, wherein the mono- and bicyclic heterocyclic groups of $R^3$ are bound via a nitrogen or carbon atom, a 1-alkyl-4-piperidinylcarbonyl or 4-alkyl-1-piperazinylcarbonyl group, wherein the mono- and bicyclic heterocyclic groups and the 1-alkyl-4-piperidinylcarbonyl and 4-alkyl-1-piperazinylcarbonyl group of $R^3$ are optionally substituted in the ring by an alkyl group with 1 to 7 carbon atoms, by an alkanoyl, dialkylamino, phenylcarbonyl, pyridinylcarbonyl, carboxyalkanoyl, carboxyalkyl, alkoxycarbonylalkyl, alkoxycarbonyl, aminocarbonyl, alkylaminocarbonyl, alkylsulphonyl, cycloalkyl, or cycloalkylalkyl group, or by a cycloalkylcarbonyl, azacycloalkylcarbonyl, diazacycloalkylcarbonyl, or oxazacycloalkylcarbonyl group optionally alkyl-substituted in the ring,
wherein the alicyclic moieties contained in these substituents contain 3 to 10 ring members and the heterocyclic moieties each contain 4 to 10 ring members, and
wherein the phenylcarbonyl and pyridinylcarbonyl substituents are optionally mono-, di-, or trisubstituted by fluorine, chlorine, or bromine atoms, by alkyl, alkoxy, methylsulphonyloxy, trifluoromethyl, hydroxy, amino, acetylamino, aminocarbonyl, aminocarbonylamino, aminocarbonylaminomethyl, cyano, carboxy, carbalkoxy, carboxyalkyl, carbalkoxyalkyl, alkanoyl, ω-(dialkylamino) alkanoyl, ω-(carboxy)alkanoyl, trifluoromethoxy, trifluoromethylthio, trifluoromethylsulphinyl, or trifluoromethylsulphonyl groups, wherein the substituents are identical or different, or $R^3$ together with $R^4$ and $Y^1$ are a 4- to 7-membered cycloaliphatic ring, in which a methylene group is optionally replaced by the group —NH— or —N(alkyl)—,
wherein a hydrogen atom bound to a nitrogen atom within the group $R^3$ is optionally replaced by a protecting group;

$R^4$ is a hydrogen atom,
an alkyl group with 1 to 4 carbon atoms, wherein an unbranched alkyl group is optionally substituted in the ω position by a phenyl, pyridinyl, diazinyl, amino, alkylamino, dialkylamino, 1-pyrrolidinyl, 1-piperidinyl, 4-methyl-1-piperazinyl, 4-morpholinyl, or hexahydro-1H-1-azepinyl group,
an alkoxycarbonyl, cyano, or aminocarbonyl group, or a free pair of electrons, if $Y^1$ is a nitrogen atom, and $R^5$ and $R^6$ are each a hydrogen atom or,
  if $Y^1$ is a carbon atom, $R^4$ together with $R^6$ also constitute another carbon-carbon bond, wherein $R^5$ is a hydrogen atom, or
  if $Y^1$ is a carbon atom, $R^4$ together with $R^6$ also constitute a further carbon-carbon bond and $R^3$ together with $R^5$ and the enclosed double bond constitute a partially hydrogenated or aromatic five- to seven-membered, mono- or bicyclic carbocyclic or heterocyclic group,
  wherein all the abovementioned alkyl and alkoxy groups as well as the alkyl groups present within the other groups mentioned contain 1 to 7 carbon atoms, unless otherwise specified, and all the abovementioned cycloalkyl groups as well as the cycloalkyl groups present within the other groups mentioned contain 5 to 10 carbon atoms, unless otherwise specified,
or a tautomer, diastereomer, or enantiomer thereof, or a pharmaceutically acceptable salt thereof.

2. The compound of the formula I according to claim 1, wherein the amino acid partial structure of formula

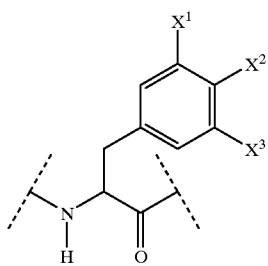

(IV)

is in the D- or (R)-configuration and, if present, the amino acid partial structure of formula

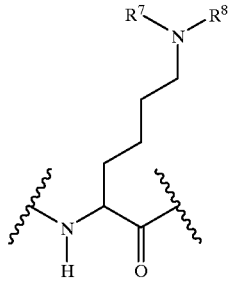

(II)

in the group A is in the L- or (S)-configuration.

3. The compound of the formula I according to claim 1, wherein:
  R is a 1-piperidinyl group substituted in the 4 position by a mono- or di-unsaturated 5- to 7-membered aza, diaza, or triaza heterocyclic group, bound via a nitrogen atom, which contains one or two carbonyl groups linked to a nitrogen atom,
    wherein the mono- or di-unsaturated 5- to 7-membered aza, diaza, or triaza heterocyclic groups of R are optionally substituted at a carbon atom by a phenyl group,
    an olefinic double bond of one of the mono- or di-unsaturated 5- to 7-membered aza, diaza, or triaza heterocyclic groups of R is optionally condensed with a benzene, pyridine, or quinoline ring or two olefinic double bonds in one of the unsaturated heterocyclic groups of R are optionally benzocondensed, and
    wherein the condensed heterocyclic groups of R are optionally mono-, di-, or trisubstituted in the carbon skeleton, and the phenyl groups contained in the condensed heterocyclic groups of R are optionally substituted, or both, by fluorine, chlorine, or bromine atoms, by $C_{1-3}$-alkyl, trifluoromethyl, $C_{1-3}$-alkoxy, hydroxy, amino, nitro, phenyl, carboxy, methoxycarbonyl, ethoxycarbonyl, aminocarbonyl, methylaminocarbonyl, hydroxyethylaminocarbonyl, (4-morpholinyl)carbonyl, (1-piperidinyl)carbonyl, or (4-methyl-1-piperazinyl)carbonyl groups, wherein the optional substituents are identical or different and multiple substitution with the three latter optional substituents is excluded, Y is a divalent group selected from

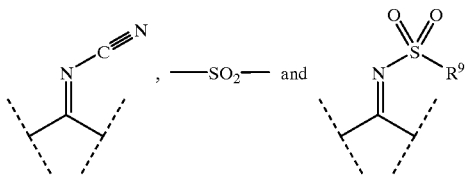

wherein $R^9$ is a $C_{1-3}$-alkyl group or a phenyl group optionally substituted by a fluorine, chlorine, or bromine atom, or by a methyl or methoxy group, $X^1$, $X^2$, and $X^3$, which are identical or different, are a hydrogen atom, a fluorine, chlorine or bromine atom, a $C_{1-3}$-alkyl, $C_{1-3}$-alkoxy, trifluoromethyl, hydroxy, amino, or acetylamino group, A is a bond or the divalent group

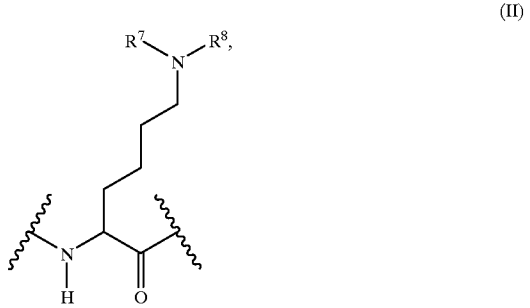

(II)

linked to the $NR^1R^2$ group of formula I via the —CO group, wherein $R^7$ and $R^8$ independently of each other in each case are a hydrogen atom or a methyl group;

$R^1$ is a hydrogen atom or
  an alkyl group with 1 to 4 carbon atoms optionally substituted in the ω position by an amino, methylamino, dimethylamino, or 4-(1-piperidinyl)-1-piperidinyl group, $R^2$ is a hydrogen atom, or a methyl or ethyl group, or $R^1$ and $R^2$ together with the enclosed nitrogen atom constitute a group of the formula (III)

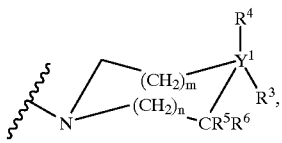

wherein

Y$^1$ is a carbon atom or, if R$^4$ is a free pair of electrons, a nitrogen atom, m is the number 0 or 1, n is the number 1 or 2, R$^3$ is a hydrogen atom, a phenyl, pyridinyl, or diazinyl group, each of which is optionally substituted in the carbon skeleton by a fluorine, chlorine, or bromine atom, or by a methyl or methoxy group, a 5- to 7-membered azacycloalkyl group, a 5- to 7-membered oxaza or diazacycloalkyl group or a 7- to 9-membered azabicycloalkyl group, wherein the abovementioned mono- and bicyclic heterocyclic groups are bound via a nitrogen or carbon atom and are optionally substituted by an alkyl group with 1 to 3 carbon atoms, by a C$_{1-4}$-alkanoyl, di-C$_{1-3}$-alkylamino, or C$_{1-3}$-alkylsulphonyl group, R$^4$ is a hydrogen atom, an alkyl group with 1 to 3 carbon atoms, wherein an unbranched alkyl group is optionally substituted in the ω position by a phenyl or pyridinyl group, or a free pair of electrons, if Y$^1$ is a nitrogen atom, and R$^5$ and R$^6$ in each case are hydrogen atoms, or a tautomer, diastereomer, or enantiomer thereof, or a pharmaceutically acceptable salt thereof.

4. The compound of the formula I according to claim 1, wherein: R is a 1-piperidinyl group which is substituted in the 4 position by a 1,3-dihydro-4-phenyl-2(2H)-oxoimidazol-1-yl, 1,3-dihydro-2(2H)-oxobenzimidazol-1-yl, 2,4(1H,3H)-dioxoquinazolin-3-yl, 1,3-dihydro-2(2H)-oxoimidazo[4,5-b]pyridin-3-yl, 3,4-dihydro-2(1H)-oxoquinazolin-3-yl, 2,3,4,5-tetrahydro-2(1H)-oxo-1,3-benzodiazepin-3-yl, 2(1H)-oxoquinolin-3-yl, 2,4-dihydro-5-phenyl-3(3H)-oxo-1,2,4-triazol-2-yl, 1,3-dihydro-2(2H)-oxoimidazo[4,5-c]quinolin-3-yl, or 5,7-dihydro-6-oxo-dibenzo[d,f][1,3]diazepin-5-yl group, wherein the bicyclic heterocyclic groups attached to the 1-piperidinyl group of R are optionally mono-, di-, or trisubstituted in the carbon skeleton, and the phenyl groups contained in the bicyclic heterocyclic groups of R are optionally substituted, or both, by fluorine, chlorine, or bromine atoms, by methyl, trifluoromethyl, methoxy, hydroxy, amino, nitro, phenyl, phenylmethyl, carboxy, methoxycarbonyl, ethoxycarbonyl, aminocarbonyl, methylaminocarbonyl, hydroxyethylaminocarbonyl, (4-morpholinyl)carbonyl, (1-piperidinyl)carbonyl, or (4-methyl-1-piperazinyl)carbonyl groups, wherein the optional substituents are identical or different and multiple substitution with the three latter optional substituents is excluded, Y is a divalent group selected from

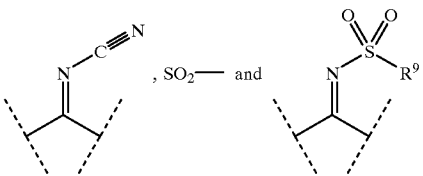

wherein R$^9$ is a methyl group or a phenyl group;

X$^1$ is a fluorine, chlorine, or bromine atom, or a methyl group;

X$^2$ is a fluorine, chlorine, or bromine atom, or a methyl, methoxy, hydroxy, or amino group;

X$^3$ is a fluorine, chlorine, or bromine atom, or a methyl group;

A is a bond or the divalent group (II)

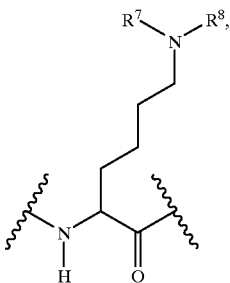

linked to the NR$^1$R$^2$ group of formula I via the —CO group, wherein R$^7$ and R$^8$ are hydrogen atoms, R$^1$ and R$^2$ together with the enclosed nitrogen atom form a group of the formula (III)

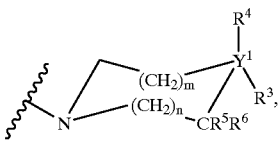

wherein

Y$^1$ is a carbon atom or, if R$^4$ is a free pair of electrons, a nitrogen atom, m is the number 1, n is the number 1, R$^3$ is a phenyl or pyridinyl group, optionally substituted in the carbon skeleton by a fluorine, chlorine, or bromine atom, or by a methyl or methoxy group, a 1-pyrrolidinyl, 1-piperidinyl, 4-(dimethylamino)-1-piperidinyl, 4-piperidinyl, or 4-morpholinyl group, wherein the nitrogen atom of the 4-piperidinyl group is optionally substituted by an alkyl group with 1 to 2 carbon atoms in each case, a hexahydro-1H-1-azepinyl, 4-methyl-1-piperazinyl or 4-ethyl-1-piperazinyl group, R$^4$ is a hydrogen atom, an alkyl group with 1 or 2 carbon atoms, or a free pair of electrons, if Y$^1$ is a nitrogen atom, and R$^5$ and R$^6$ are each hydrogen atoms, or a tautomer, diastereomer, or enantiomer thereof, or a pharmaceutically acceptable salt thereof.

5. A pharmaceutical composition comprising a compound according to one of claims 1, 2, 3, or 4 and a pharmaceutically acceptable carrier.

6. A method for the acute treatment or prophylaxis of migraine or cluster headaches, the method comprising administering to a host in need of such treatment or prophylaxis a therapeutically or prophylactically effective amount of a compound in accordance with one of claims 1, 2, 3, or 4.

7. A method for the treatment of non-insulin-dependent diabetes mellitus, the method comprising administering to a host in need of such treatment a therapeutically effective amount of a compound in accordance with one of claims 1, 2, 3, or 4.

8. A method for the treatment of inflammation, the method comprising administering to a host in need of such treatment a therapeutically effective amount of a compound in accordance with one of claims 1, 2, 3, or 4.

9. A method for the treatment of allergic rhinitis, the method comprising administering to a host in need of such treatment a therapeutically effective amount of a compound in accordance with one of claims 1, 2, 3, or 4.

10. A method for the treatment of asthma, the method comprising administering to a host in need of such treatment a therapeutically effective amount of a compound in accordance with one of claims 1, 2, 3, or 4.

11. A method for the treatment of a disease characterized by excessive vasodilatation and consequent reduction in blood-flow, the method comprising administering to a host in need of such treatment a therapeutically effective amount of a compound in accordance with one of claims 1, 2, 3, or 4.

12. A method for the treatment of morphine tolerance, the method comprising administering to a host in need of such treatment a therapeutically effective amount of a compound in accordance with one of claims 1, 2, 3, or 4.

13. A method for the treatment of menopausal hot flashes, the method comprising administering to a host in need of such treatment a therapeutically effective amount of a compound in accordance with one of claims 1, 2, 3, or 4.

* * * * *